US012690966B2

(12) United States Patent
Lv et al.

(10) Patent No.: US 12,690,966 B2
(45) Date of Patent: Jul. 28, 2026

(54) MITRAL VALVE CLIP HAVING LOCKING MECHANISM

(71) Applicant: Jenscare Scientific Co., Ltd., Zhejiang (CN)

(72) Inventors: Shiwen Lv, Zhejiang (CN); Zhi Chen, Zhejiang (CN); Kan Lu, Zhejiang (CN); Lei Wu, Zhejiang (CN)

(73) Assignee: Jenscare Scientific Co., Ltd., Zhejiang (CN)

( * ) Notice: Subject to any disclaimer, the term of this patent is extended or adjusted under 35 U.S.C. 154(b) by 535 days.

(21) Appl. No.: 18/268,120

(22) PCT Filed: Nov. 26, 2021

(86) PCT No.: PCT/CN2021/133489
§ 371 (c)(1),
(2) Date: Jun. 16, 2023

(87) PCT Pub. No.: WO2022/127561
PCT Pub. Date: Jun. 23, 2022

(65) Prior Publication Data
US 2024/0033084 A1 Feb. 1, 2024

(30) Foreign Application Priority Data
Dec. 18, 2020 (CN) .......................... 202011511245.2

(51) Int. Cl.
*A61F 2/24* (2006.01)
(52) U.S. Cl.
CPC ...... *A61F 2/246* (2013.01); *A61F 2210/0014* (2013.01)
(58) Field of Classification Search
CPC ........... A61F 2/24; A61F 2/2442; A61F 2/246
See application file for complete search history.

(56) References Cited

U.S. PATENT DOCUMENTS

2010/0022823 A1 1/2010 Goldfarb et al.
2018/0146964 A1 5/2018 Garcia et al.

FOREIGN PATENT DOCUMENTS

| CN | 106491245 A | 3/2017 |
| CN | 111449805 A | 7/2020 |
| CN | 211325891 U | * 8/2020 |

OTHER PUBLICATIONS

1st Office Action for Chinese Patent Application No. 202011511245.2 issued Dec. 21, 2024.

* cited by examiner

*Primary Examiner* — Ashley L Fishback
(74) *Attorney, Agent, or Firm* — Wood, Phillips, Katz, Clark & Mortimer

(57) ABSTRACT

Valve clip having locking mechanism includes first clamping arm, second clamping arm, linking member, push-pull device and locking device. The locking device fitted with the linking member and includes locking head and self-locking rod. The linking member hinged to each of the first clamping arm and the second clamping arm which include a long arm whose end is hinged to the push-pull device and a short arm whose end is provided with a locking portion. When the push-pull device operated to enlarge opening angle between the long arms of the first clamping arm and the second clamping arm in an open state, the locking portions of the first clamping arm and the second clamping arm are in a staggered fit state; and when to narrow the opening angle in a closed state, the locking device moved to cause the locking head to be fitted and locked to the locking portions.

18 Claims, 24 Drawing Sheets

42

41

42

41

41

311

312

311

312

8

4

5

MITRAL VALVE CLIP HAVING LOCKING MECHANISM

CROSS-REFERENCE TO RELATED APPLICATIONS

This is a national stage application filed under 37 U.S.C. 371 based on International Patent Application No. PCT/CN2021/133489 filed on Nov. 26, 2021, which claims priority to Chinese Patent Application No. 202011511245.2 filed on Dec. 18, 2020, the disclosures of both of which are incorporated herein by reference in their entireties.

TECHNICAL FIELD

The present application relates to the field of medical instruments, and in particular to, a valve clip having a locking mechanism.

BACKGROUND

The mitral valve has a complex anatomical structure and includes the leaflets, annulus, chordae tendineae and papillary muscles, which play important roles in maintaining the function of the left ventricle and the right ventricle, respectively. Any disease that adversely affects the structural integrity and function normality of the leaflets, annulus, chordae tendineae, papillary muscles and the left ventricle may lead to severe mitral regurgitation (MR), which may cause left ventricular failure, pulmonary hypertension, atrial fibrillation, stroke and death. According to recent epidemiological survey data in developed western countries such as the United States, the leading type of valvular disease in the elderly population older than 65 years is mitral regurgitation. Currently, although there is no definitive epidemiological survey data in China, the number of patients with the mitral regurgitation in China is indisputably huge as the population ages. The mitral regurgitation may be divided into a degenerative MR and a functional MR. The degenerative MR is caused by pathological changes of one or more of the leaflets, the annulus, the chordae tendineae, and the papillary muscles. The functional MR is typically left ventricular dysfunction, such as dilatation of annulus, but the mitral valve is generally normal.

At present, treatment methods of the MR mainly include drug therapy, surgery and interventional therapy. The drug therapy may only improve the symptoms of the patient and cannot prolong the survival time of the patient. The surgery primarily includes valve repair or valve replacement, is recognized as the best treatment method for the mitral regurgitation, and has been proved to be capable of alleviating the symptoms of the patient and prolonging the life of the patient. However, for many high-risk patients with advanced age and multiple system diseases, the risk of the surgery is high, the survival benefit is low. According to data from European, a success rate of the surgeries of such patients is only 50%, and a surgical success rate of the surgeries of patients with severe functional MR is as low as 16%. Thus, the transcatheter interventional mitral valve repair and replacement could theoretically benefit high-risk patients who lost the opportunity for surgery. The interventional therapy is a therapy in which an artificial implant is loaded onto a delivering system in vitro, the artificial implant is delivered to the mitral annulus along a vascular path or through cardiac apex puncturing, and then the artificial implant is released and fixed to replace the function of a native valve completely or partially. Currently, the interventional therapy of the mitral valve has become one of the hot spots of research in related fields, and many products are under development. However, the development of interventional instrument for the mitral valve faces many special difficulties due to the problems such as the complexity of the mitral valve itself and the surrounding structures.

A method for fixing a tissue is provided in patent CN103826548A, the method includes as follows. An implantable fixation device is provided, the implantable fixation device includes a pair of fixation elements, each of the pair of fixation elements has a first end, a free end opposite to the first end, and an engagement surface between the first end and the free end for engaging the tissue. The first ends are movably coupled together such that the fixation elements are movable between a closed position in which the engagement surfaces face each other and a first open position in which the engagement surfaces are positioned away from each other. The locking mechanism in this patent includes one or more wedging elements, such as rolling elements. The rolling elements include a pair of barbells arranged on opposite sides of a stud, the barbells are operated by hooked ends of a release harness. When an upward force is applied to the harness by a lockline, the hooked ends raise the barbells against a spring. This draws the barbells up along a side wall or a sloping surface which unwedges the barbells from against the stud. By releasing the upward force on the barbells by the hooked ends, the spring forces the barbells downwards and wedges the barbells between the sloping surface and the stud. This restricts motion of the stud, which in turn locks an actuation mechanism and therefore the distal elements in place. The technical drawbacks of the locking mechanism of MitraClip in this invention lie in that: the design of the locking structure is relatively complex, and it is required the rolling elements, the spring, the lockline, the wedging elements located between the sloping surface and the stud to cooperate with each other to achieve the locking, therefore the requirement on the assembling process is high. In an initial state, the spring is in a stressed and deformed state, and the original state may be restored when the lockline is released, so the locking structure is not reversible, thus if an operation error occurs before the clamping of the valve is completed during the surgery, the locking mechanism cannot be unlocked, which means that the surgery fails. The implantation instrument is retained within the body after the surgery, and the spring is fatigued after being stressed for a long time, whereby the clamping force for the leaflets is adversely affected, so the unlocking mechanism has potential safety hazards.

A valve clip device is disclosed in patent CN201880066104.9, which includes a spacer member configured to be disposed between leaflets of a native heart valve that is located between a first chamber and a second chamber of the heart. The prosthetic device further includes multiple anchor members coupled to the spacer member and configured to catch the leaflets between respective anchor members and the spacer member such that the prosthetic device is retained between the leaflets. The spacer member is configured to provide a flow path through the prosthetic device between the first chamber and the second chamber when the leaflets are caught between the anchor members and the spacer member such that blood can flow regurgitatively from the second chamber to the first chamber through the spacer member. In the technical solution in this patent, a premolded metal material is used to clamp and fix native leaflets, which, simplifies its transmission system, but due to lacking of reliable locking device, and moreover, the continuous contracting and relaxing of the heart, renders the native leaflets being apt to slip off from between the spacer member and the anchor members, and moreover, the pre-molded metal material is used to clamp and fix the native leaflets, which is apt to cause damage due to fatigue and adversely affects the service life of the valve clip.

In summary, since the locking structure in the conventional technology has a relatively complex design, has extremely high requirements on the assembling process, and moreover, the elastic sheet may be fatigued after a long time service to adversely affect the clamping force, therefore, it is in demand for a locking mechanism which has a relatively simplified structural design, is convenient to assemble, and can maintain the clamping force for a long time.

SUMMARY

Aspects of the present application are to provide a valve clip having a locking mechanism, and the valve clip has the advantages of being simple in structure, having low requirements on the assembling process, and being capable of maintaining a clamping force for a long time.

In order to address the above-described technical issues, the present application provides the following technical solutions. A valve clip having a locking mechanism includes a first clamping arm, a second clamping arm, a linking member, a push-pull device and a locking device. The locking device is partially fitted with the linking member. The locking device includes a locking head and a self-locking rod. The linking member is hinged to each of the first clamping arm and the second clamping arm. The first clamping arm includes a first long arm and a first short arm and the second clamping arm includes a second long arm and a second short arm, an end of each of the first long arm and the second long arm is hinged to the push-pull device, an end of the first short arm is provided with a first locking portion, and an end of the second short arm is provided with a second locking portion. When the push-pull device is operated to cause an opening angle between the first long arm of the first clamping arm and the second long arm of the second clamping arm to become larger and be in an open state, the first locking portion of the first clamping arm and the second locking portion of the second clamping arm are partially in a staggered fit state. When the push-pull device is operated to cause the opening angle between the first long arm of the first clamping arm and the second long arm of the second clamping arm to become smaller and be in a closed state, the locking device is moved to cause the locking head to be fitted with and locked to the first locking portion and the second locking portion.

The present application may also be further implemented by the following technical solutions.

In an embodiment, a locking region is formed between the linking member and the first locking portion and the second locking portion, and the size of the locking region changes with the change of the opening angle between the first clamping arm and the second clamping arm. The locking region gradually becomes larger when the opening angle between the first clamping arm and the second clamping arm gradually becomes smaller. When the locking head enters the locking region and is locked to and fitted with the first locking portion and the second locking portion, the valve clip is locked.

In an embodiment, each of the first long arm and the second long arm is provided with a bias structure, and the bias structure is arranged to divide the respective first long arm and the respective second long arm into a fit portion and a transmission portion. When the opening angle between the first long arm of the first clamping arm and the second long arm of the second clamping arm becomes smaller to be in the closed state, the fit portion is located closer than the transmission portion to the central axis of the valve clip.

In an embodiment, a rotatable structure is provided between the self-locking rod and the locking head to enable the self-locking rod and the locking head to rotate relative to each other.

In an embodiment, the linking member includes a linking block and connection lugs arranged on the linking block, the linking block is connected to the locking device, and the connection lugs are hinged to the first clamping arm and the second clamping arm, respectively.

In a preferred embodiment, the linking member is an arc-shaped structure or a "V"-shaped structure. With this design, the length of the valve clip when in a preloaded state can be shortened.

In a preferred embodiment, the connection lugs are axially symmetrical about an axis of the linking block.

In a preferred embodiment, the linking block is provided with a mounting recess, at least part of the locking head is always arranged within the mounting recess, and the mounting recess is arranged to restrict the locking head from rotating in a circumferential direction. With this design, in a case where the locking head is configured to be an irregular-shaped structure, in the process that the self-locking rod is operated to drive the locking head to move axially till being fitted with and locked to the first locking portion and the second locking portion, the mounting recess restricts the locking head from rotating in the circumferential direction, and therefore the locking head enters the locking region according to the predetermined position and is fitted with the first locking portion and the second locking portion.

In a preferred embodiment, the linking block is provided with a through hole in the axial direction, and the mounting recess is arranged on a distal end side of the through hole.

In an embodiment, the locking head is restrained by the mounting recess from moving towards a proximal end, and the mounting recess has a diameter greater than the diameter of the through hole.

In an embodiment, the self-locking rod is solid or hollow.

In a preferred embodiment, when the locking region formed in the first locking portion and the second locking portion is a wedge-shaped structure or the locking region formed in the first locking portion and the second locking portion is a tapered structure, the locking head is correspondingly configured to be a wedge-shaped structure or a tapered structure. When both the locking region and the locking head are the wedge-shaped structure or the tapered structure, the acting force of locking is stronger and the valve clip is more stable and reliable.

In an embodiment, the locking head is a stent-shaped self-expansion structure, and the locking head is fitted with the first locking portion and the second locking portion to be locked to the first locking portion and the second locking portion.

In an embodiment, the locking head is a tapered structure, or a shuttle-shaped structure, or a diamond-shaped structure, or a prismatic structure, or an arrow-shaped structure.

In a preferred embodiment, the locking head is configured to be hollow, the locking head is made of an elastic metal material, and is formed therein with a hollow region, and the hollow region serves as a buffer region. After the valve clip is implanted into the heart, the first clamping arm and the second clamping arm are subjected to a certain degree of stress due to the compression and relaxation of the heart valve itself, whereby the degrees of closing between the push-pull device and the first clamping arm and between the push-pull device and the second clamping arm are adversely affected, and a certain degree of regurgitatively flowing occurs. In the case where the locking head is made of the elastic metal material and the locking head is formed therein with the buffer region, the first long arm of the first clamping arm and the second long arm of the second clamping arm are subjected to a stress caused by the movement of the valve itself and then the stress is transferred to the first short arm and the second short arm, and subsequently the stress applied to the first short arm and the second short arm is transferred to the locking head, whereby the locking head is deformed in a certain degree, and breaks down the stress received by it, thereby always guaranteeing the clamping force and the tightness between the push-pull device and the first clamping arm and between the push-pull device and the second clamping arm, and avoiding the regurgitation.

In an embodiment, each of the first short arm and the second short arm is in an arc shape or an "L" shape, and when the opening angle between the first clamping arm and the second clamping arm becomes larger, the first locking portion of the first clamping arm is fitted with the second locking portion of the second clamping arm in a staggered manner. The first locking portion and the second locking portion are designed to be arc-shaped segments or in "L" shapes, which is beneficial to increasing force arms of the first locking portion and the second locking portion and enhancing the acting force of locking, and moreover, the manner of staggered fit between the first locking portion and the second locking portion is beneficial to saving the space for loading.

In an embodiment, the linking member is provided with an anti-retreat structure which is fitted with the self-locking rod. The anti-retreat structure can enhance the stability of the locking device and ensure the locking effect for a long time.

In a preferred embodiment, the anti-retreat structure is screw threads or a recess.

In an embodiment, the push-pull device includes leaflet catching devices, a leakage-proof tubular member, and a first linkage rod and a second linkage rod. The first linkage rod and the second linkage rod are hinged to the leakage-proof tubular member and are arranged on left and right sides of the leakage-proof tubular member, respectively, and the first linkage rod and the second linkage rod are hinged to the first clamping arm and the second clamping arm, respectively. The leaflet catching devices are arranged on the first linkage rod and the second linkage rod respectively. The leaflet catching devices each have a preset shape, and the leaflet catching devices closely fit against the linkage rods respectively in a natural state. The leaflet catching devices, when being preloaded, always fit against the leakage-proof tubular member. When the valve clip catches the leaflets, the leaflet catching devices restore the preset shape to clamp the leaflets.

In a preferred embodiment, the leaflet catching devices may be controlled separately to clamp and anchor a single leaflet, whereby the operational difficulty is reduced.

In an embodiment, the first locking portion includes multiple first arc-shaped struts and the second locking portion includes multiple second arc-shaped struts, and the first arc-shaped struts and the second arc-shaped struts are distributed in a comb-like shape. When the opening angle between the first clamping arm and the second clamping arm becomes larger, the first arc-shaped struts of the first clamping arm are fitted with the second arc-shaped struts of the second clamping arm in a staggered manner, and the multiple first arc-shaped struts and second arc-shaped struts distributed in the comb-like shape facilitate increasing force acting points of the first short arm and the second short arm, to allow the locking to be more stable and reliable.

In a preferred embodiment, an end of each of the first arc-shaped struts and second arc-shaped struts is curved inwardly, and the ends of the arc-shaped struts provide force receiving points to the locking device when the first clamping arm and the second clamping arm are closed.

In an embodiment, the cross section of each of the first long arm and the second long arm is in an internally-concaved shape. With such a design, when the valve clip is in the closed state, the first long arm and the second long arm have a certain wrapping effect on the leakage-proof tubular member, so that the leakage-proof effect of the leakage-proof tubular member is better. Moreover, the configuration of the internally concaved shape renders significant reduction of the weight of the first long arm and the second long arm, therefore, the slippage of the valve clip in the heart due to the excessive weight is effectively avoided, the stability of anchoring of the valve clip in the heart is facilitated, and the native leaflets may not be excessively torn and the intracardiac tissues may not be injured accordingly.

In an embodiment, an end, connected to the push-pull device, of each of the first long arm and the second long arm is provided with a circular arc-shaped buffer segment. With this design, when the valve clip catches the leaflets and completes the clamping, the circular arc-shaped buffer segments may protect the native leaflets from being injured.

In an embodiment, each of the first clamping arm and the second clamping arm is provided with a fit structure at a hinge point. With the fit structure being designed, the first short arm and the second short arm drive the first long arm and the second long arm respectively in the manner of levering with the hinge point as a fulcrum, therefore the force received at the hinge point is relatively large upon locking, and moreover, the fit structure may increase the area of contact with the linking member, to allow the locking torque to be more balanced.

Compared with the conventional technology, the present application has the following advantages.

1. Different from the conventional technology, in the present application, when the push-pull device is operated to cause an opening angle between the first long arm of the first clamping arm and the second long arm of the second clamping arm to become larger and be in an open state, the first locking portion of the first clamping arm and the second locking portion of the second clamping arm are partially in a staggered fit state, without interfering/adversely affecting the size of the opening angle between the first clamping arm and the second clamping arm, which facilitates catching and clamping the leaflet, and when the valve clip is required to be locked, the locking device is moved to allow the locking head to be fitted with and locked to the first locking portion and the second locking portion, thus, the locking is performed. By means of the lever principle, torque balance is reached between the end of the locking device and the first locking portion and the second locking portion, so that the opening angle between the first clamping arm and the second clamping arm is controlled to not be increased, and the locking effect is achieved. Moreover, the locking structure achieves locking mechanically, the structure is simple, the operation is simple and convenient without fatigue risk, and the clamping effect thereof may be ensured for a long time.

2. Different from the conventional technology, in the present application, each of the first short arm and the second short arm is in an arc shape or "L" shape. With this design, the first arc-shaped segments and the second arc-shaped segments may increase the force arms of the first locking portion and the second locking portion, and further ensure the acting force of locking of the valve clip, so that the locking state of the valve clip is more stable and reliable, and moreover, the staggered fit manner is beneficial to saving the space for loading.

3. Different from the conventional technology, in the present application, the linking member is provided with the mounting recess, at least part of the locking head is always arranged within the mounting recess, and the mounting recess is arranged to restrict the locking head from rotating in the circumferential direction. With this design, in a case where the locking head is configured to be an irregular-shaped structure, in the process that the self-locking rod is operated to drive the locking head to move axially till being fitted with and locked to the first locking portion and the second locking portion, the mounting recess restricts the locking head from rotating in the circumferential direction, and therefore the locking head enters the locking region according to the predetermined position and is fitted with the first locking portion and the second locking portion. Moreover, in the case where the linking member is provided with the mounting recess, the weight of the valve clip may be reduced, whereby the valve clip is effectively prevented from slipping in the heart due to excessive weight, and the stability of anchoring the valve clip in the heart is facilitated.

4. Different from the conventional technology, the cross section of each of the first long arm and the second long arm in the present application is in an internally-concaved shape. With such a design, when the valve clip is in the closed state, the first long arm and the second long arm have a certain wrapping effect on the leakage-proof tubular member, so that the leakage-proof effect of the leakage-proof tubular member is better. Moreover, the configuration of the internally concaved shape renders significant reduction of the weight of the first long arm and the second long arm, therefore, the slippage of the valve clip in the heart due to the excessive weight is effectively avoided, the stability of anchoring of the valve clip in the heart is facilitated, and the native leaflets may not be excessively torn and the intracardiac tissues may not be injured accordingly.

5. Different from the conventional technology, in the present application, the locking head is the stent-shaped self-expansion structure, the locking head is formed therein with a hollow region, and the hollow region serves as a buffer region. After the valve clip is implanted into the heart, the first clamping arm and the second clamping arm are subjected to a certain degree of stress due to the compression and relaxation of the heart valve itself, whereby the degrees of closing between the push-pull device and the first clamping arm and between the push-pull device and the second clamping arm are adversely affected, and a certain degree of regurgitatively flowing occurs. In the case where the locking head is made of the elastic metal material and the locking head is formed therein with the buffer region, the first long arm of the first clamping arm and the second long arm of the second clamping arm are subjected to a stress caused by the movement of the valve itself and then the stress is transferred to the first short arm and the second short arm, and subsequently the stress applied to the first short arm and the second short arm is transferred to the locking head, whereby the locking head is deformed in a certain degree, and breaks down the stress received by it, thereby always guaranteeing the clamping force and the tightness between the push-pull device and the first clamping arm and between the push-pull device and the second clamping arm, and avoiding the regurgitation.

6. Different from the conventional technology, in the present application, the bias structure is provided, and the bias structure is configured such that when the opening angle between the first long arm of the first clamping arm and the second long arm of the second clamping arm becomes smaller and be in the closed state, the fit portion is located closer to a central axis of the valve clip than the transmission portion, so that when the valve clip is closed, the first long arm and the second long arm may closely fit the leakage-proof tubular member, whereby the closing force of the valve clip is further ensured and the leakage-proof effect is also improved.

BRIEF DESCRIPTION OF DRAWINGS

FIGS. 3c~3g are various embodiments of the locking block.

Figure 1A:
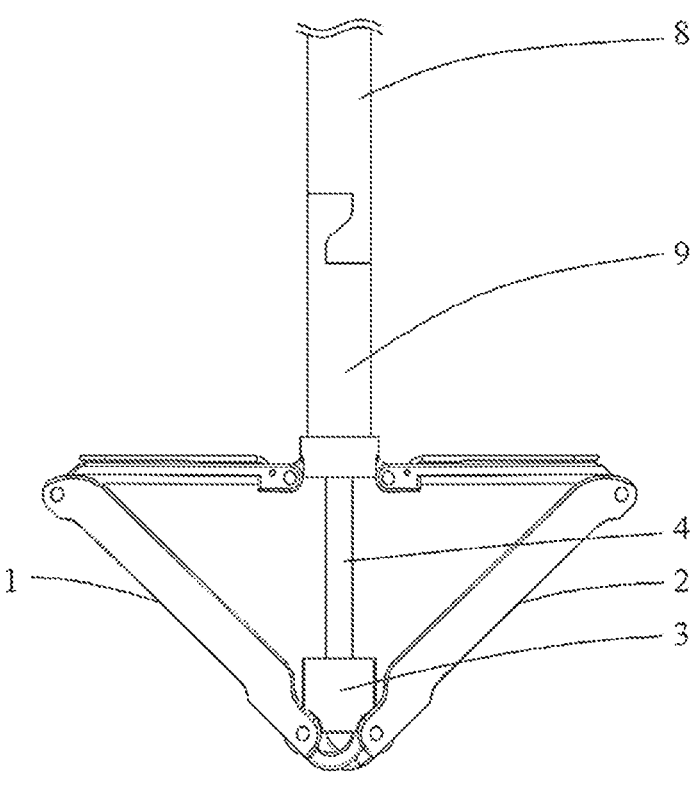
FIGS. 1a~1d are schematic diagrams showing a process in which a valve clip according to the present application implements locking.
Figure 1B:
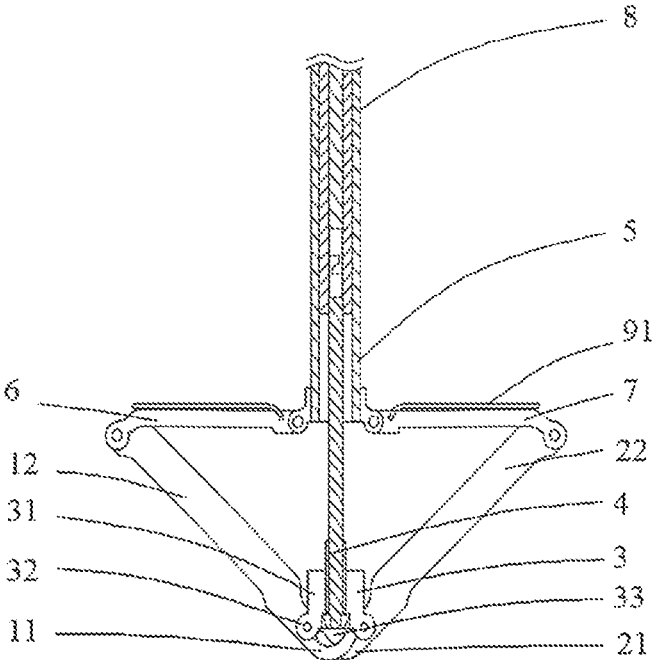

The names of the components indicated by the reference numerals in the drawings are as follows:

1—First clamping arm,
11—First short arm,
12—First long arm,
13—Fit structure,

111—First locking portion,
121—Circular arc-shaped buffer segment,
122—Bias structure,
123—Fit portion,
124—Transmission portion,
1111—First arc-shaped segment,
1112—First arc-shaped strut,
2—Second clamping arm,
21—Second short arm,
211—Second locking portion,
22—Second long arm,
2111—Second arc-shaped segment,
3—Linking member,
31—linking block,
311—Through hole,
312—Mounting recess,
32—Connection lug,
33—Locking region,
34—Anti-retreat structure,
4—Locking device,
41—Locking head,
42—Self-locking rod,
43—Rotatable structure,
431—Groove,
432—Boss,
5—Leakage-proof tubular member,
6—First linkage rod,
7—Second linkage rod,
8—Delivering catheter,
9—Push-pull device,
91—Leaflet catching device.

DETAILED DESCRIPTION

The present application is described in further detail below with reference to the drawings and embodiments.

A proximal end described in the present application refers to an end near a surgical operator, and a distal end refers to an end away from the surgical operator.

First Embodiment

In the treatment of the mitral valve disease, as shown in FIGS. 1a, 1b, 1c and 1d, a valve clip having a locking mechanism includes a first clamping arm 1, a second clamping arm 2, a linking member 3, a push-pull device 9 and a locking device 4. The locking device 4 is partially fitted with the linking member 3. The locking device 4 includes a locking head 41 and a self-locking rod 42. The linking member 3 is hinged to each of the first clamping arm 1 and the second clamping arm 2. The first clamping arm 1 includes a first long arm 12 and a first short arm 11 and the second clamping arm 2 includes a second long arm 22 and a second short arm 21, an end of the first long arm 12 and an end of the second long arm 22 are hinged to the push-pull device 9, and an end of the first short arm 11 is provided with a first locking portion 111, and an end of the second short arm 21 is provided with a second locking portion 211. When the push-pull device 9 is operated to cause an opening angle between the first long arm 12 of the first clamping arm 1 and the second long arm 22 of the second clamping arm 2 to become larger and be in an open state, the first locking portion 111 of the first clamping arm 1 and the second locking portion 211 of the second clamping arm 2 are partially in a staggered fit state. When the push-pull device 9 is operated to cause the opening angle between the first long arm 12 of the first clamping arm 1 and the second long arm 22 of the second clamping arm 2 to become smaller and be in a closed state, the locking device 4 is moved to cause the locking head 41 to be fitted with and locked to the first locking portion 111 and the second locking portion 211.

The composition and connection manner of the components of the valve clip having the locking mechanism of the present application are described in detail below with reference to the drawings.

In this embodiment, a locking region 33 is formed between the linking member 3 and the first locking portion 111 and the second locking portion 211, and the size of the locking region 33 changes with the change of the opening angle between the first clamping arm and the second clamping arm. The locking region 33 gradually becomes larger when the opening angle between the first clamping arm 1 and the second clamping arm 2 gradually becomes smaller. When the locking head 41 enters the locking region 33 and is locked to and fitted with the first locking portion 111 and the second locking portion 211, the valve clip is locked, as shown in FIGS. 2e and 2f.

Figure 2A:
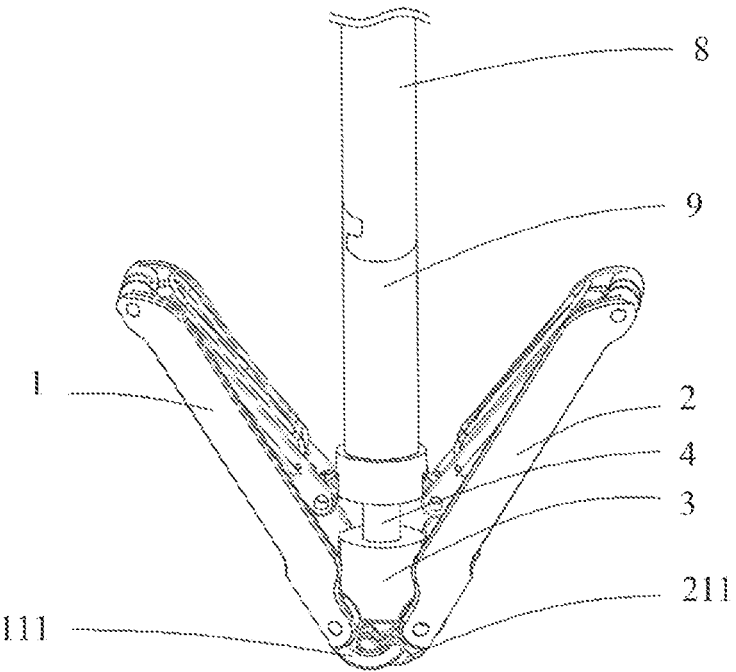
FIGS. 2a~2h are schematic structural diagrams of a first clamping arm, a second clamping arm, a first locking portion, a second locking portion and first arc-shaped struts according to the present application.
Figure 2B:
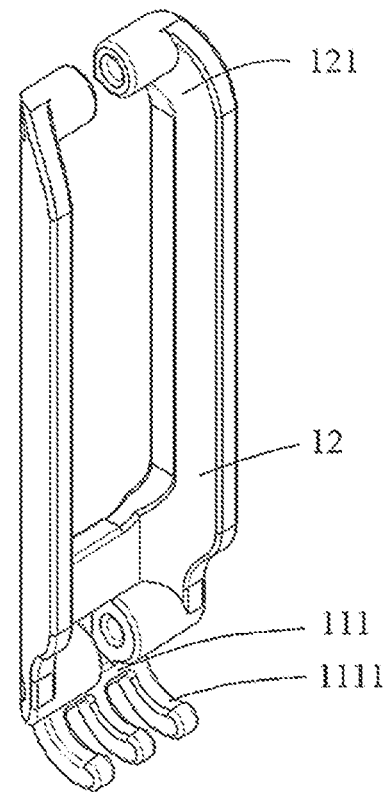
Figure 2C:
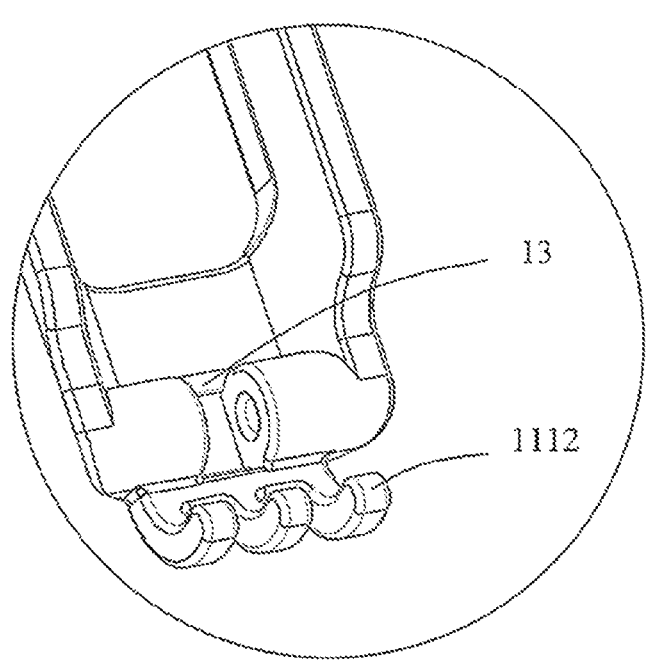
Figure 2D:
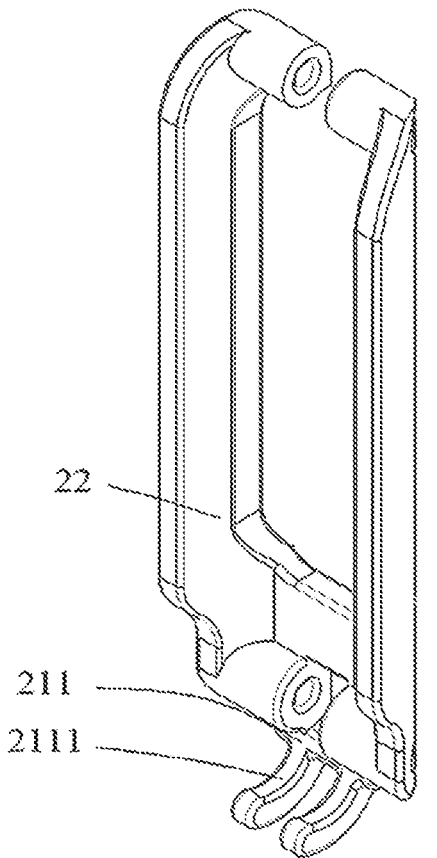
Figure 2E:
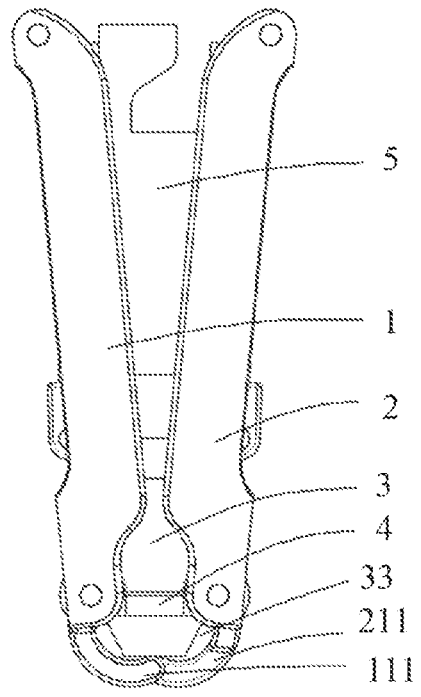
Figure 2F:
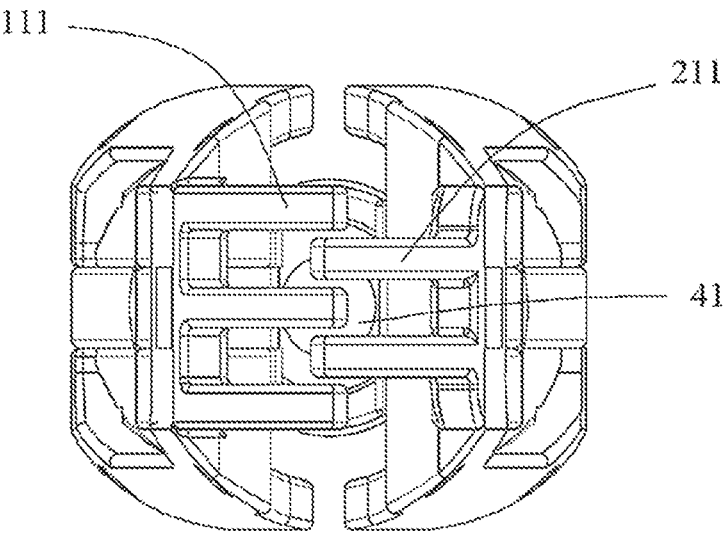
Figure 2G:
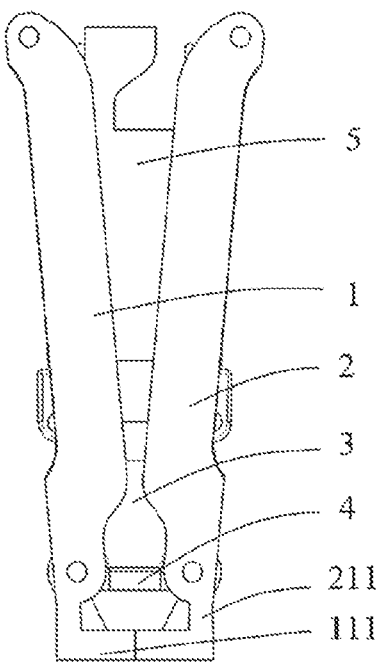
Figure 2H:
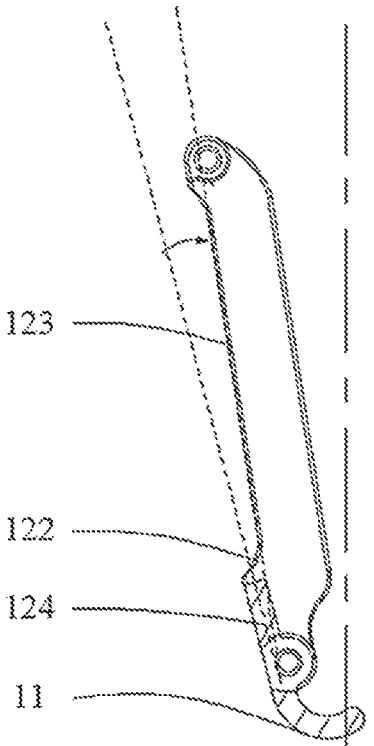

In this embodiment, the first long arm 12 is provided with a bias structure 122, as shown in FIG. 2h, the bias structure 122 is arranged to divide the first long arm 12 into a fit portion 123 and a transmission portion 124. It should be noted that, in the FIG. 2h, only the first long arm 12 divided into the fit portion 123 and the transmission portion 124 is shown as an example, the same arrangement is applied to the second long arm 22. When the opening angle between the first long arm 12 of the first clamping arm 1 and the second long arm 22 of the second clamping arm 2 becomes smaller to be in the closed state, the fit portion 123 is located closer to a central axis of the valve clip than the transmission portion 124. With this design, when the valve clip is in the closed state, the first long arm 12 and the second long arm 22 may closely fit the push-pull device 9, so that the clamping effect is further improved, and also, the leakage-proof function is improved.

In this embodiment, the first locking portion 111 includes first arc-shaped segments 1111 and the second locking portion 211 includes second arc-shaped segments 2111, as shown in FIGS. 2a, 2b and 2d, and when the opening angle between the first clamping arm 1 and the second clamping arm 2 becomes larger, the first arc-shaped segments 1111 of the first clamping arm 1 are buckled with the second arc-shaped segments 2111 of the second clamping arm 2 in a staggered manner. The first locking portion 111 is designed to be the first arc-shaped segments 1111, which is beneficial to increasing a force arm of the first locking portion 111 and enhancing the acting force of locking, and moreover, the staggered buckled manner is beneficial to saving the space for loading. In the same principle, the first locking portion 111 and the second locking portion 211 may also be configured in an "L" shape, as shown in FIG. 2g.

In this embodiment, the first locking portion 111 includes multiple first arc-shaped struts 1112, as shown in FIG. 2c. When the opening angle between the first clamping arm 1 and the second clamping arm 2 becomes larger, the first arc-shaped struts 1112 of the first clamping arm 1 are buckled with second arc-shaped struts of the second clamping arm 2 in a staggered manner. The multiple first arc-shaped struts 1112 and the second arc-shaped struts facilitate increasing of action points of forces received by the first short arm 11 and the second short arm 21, so that the locking is more stable and reliable.

In this embodiment, the first clamping arm 1 has three first arc-shaped struts 1112, and the second clamping arm 2 has two second arc-shaped struts, as shown in FIG. 2c. Ends of the first arc-shaped struts 1112 touch the locking head 41 on the premise that the strengths of the first arc-shaped struts 1112 are ensured.

In this embodiment, the first clamping arm is provided with a fit structure 13 at a hinge point, as shown in FIG. 2c. With the fit structure 13 being designed, the first short arm 11 drives the first long arm 12 in the manner of levering with the hinge point as a fulcrum, therefore the force received at the hinge point is relatively large upon locking, and moreover, the fit structure 13 may increase the area of contact with the linking member 3, to allow the locking torque to be more balanced. It should be noted that, in the FIG. 2c, only the first clamping arm provided with the fit structure 13 is shown as an example, the same arrangement is applied to the second clamping arm.

Figure 3A:
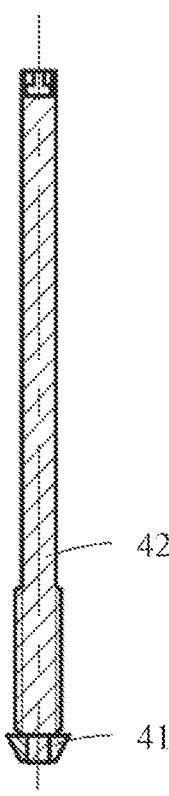
FIGS. 3a~3g are schematic structural diagrams of a locking device and a locking block according to the present application, where
Figure 3B:
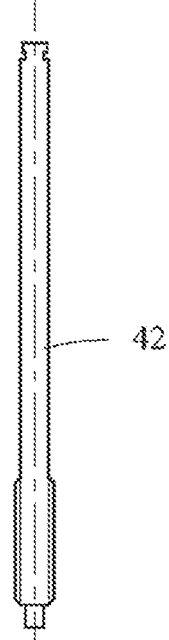
Figure 3C:
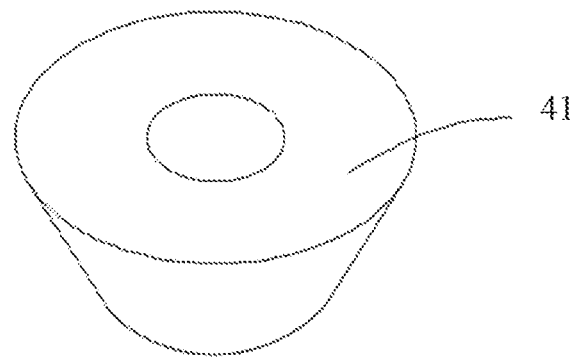
Figure 3D:
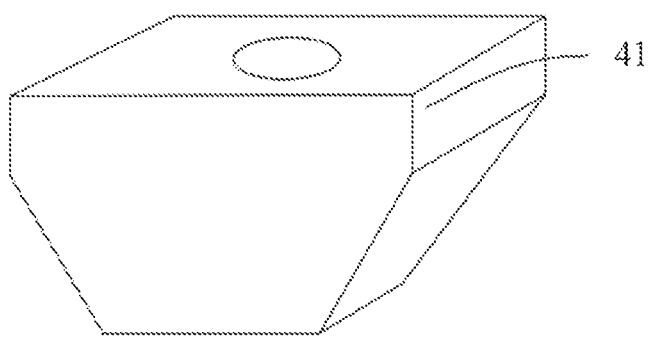
Figure 3E:
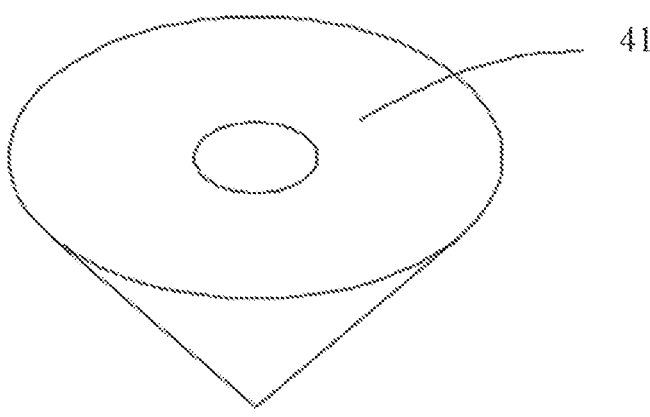
Figure 3F:
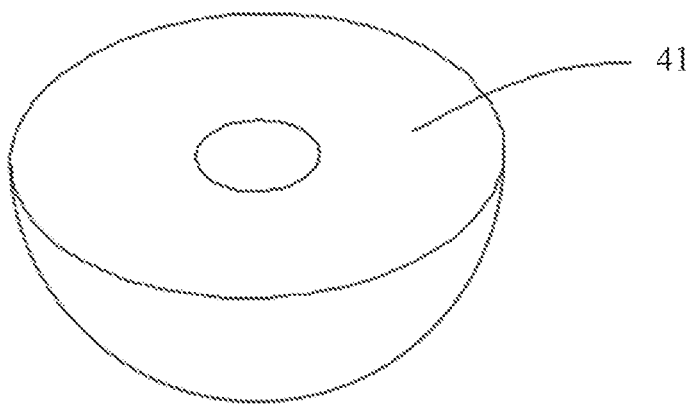
Figure 3G:
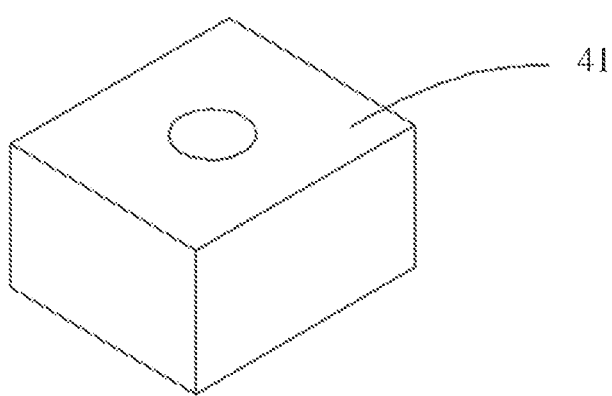

In this embodiment, the locking device 4 includes a locking head 41 and a self-locking rod 42, as shown in FIGS. 3a and 3b. The locking head 41 is in a trapezoid fit or wedge fit or taper fit or circular surface fit or cube fit with the first locking portion 111 of the first short arm 11 and the second locking portion 211 of the second short arm 21, as shown in FIGS. 3c, 3d and 3g.

Figure 4A:
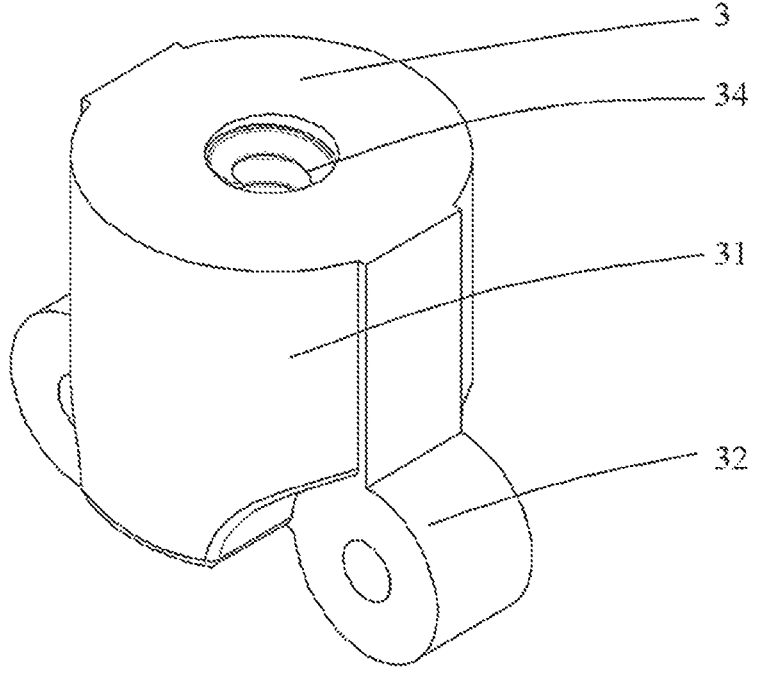
FIGS. 4a~4d are schematic structural diagrams of a linking member according to the present application.
Figure 4B:
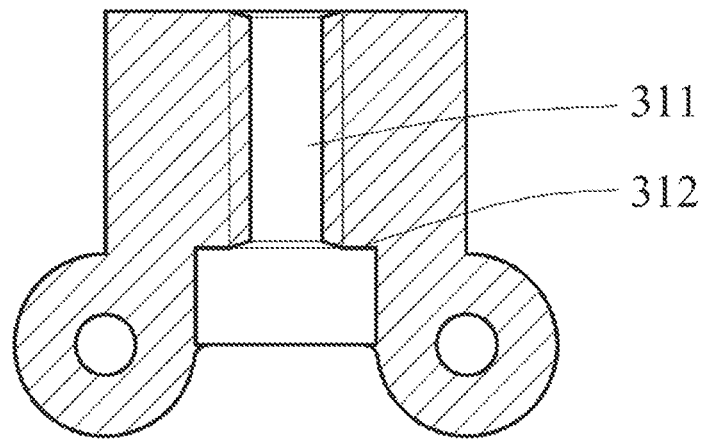

In this embodiment, the linking member 3 includes a linking block 31 and connection lugs 32 arranged on the linking block 31, as shown in FIGS. 4a and 4b, the linking block 31 is connected to the locking device 4, and the connection lugs 32 are hinged to the first clamping arm 1 and the second clamping arm 2, respectively.

Figure 4C:
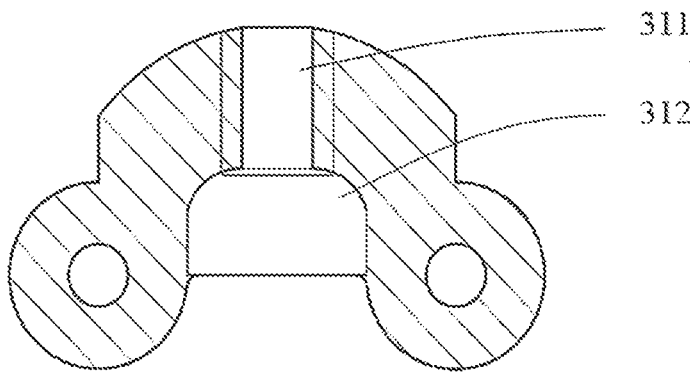
Figure 4D:
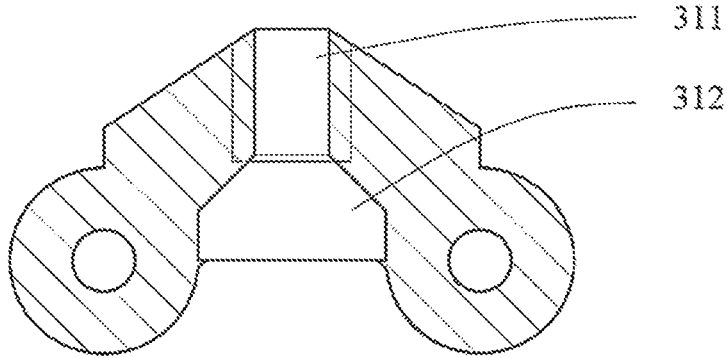

In this embodiment, the linking member 3 may be an arc-shaped structure or a "V"-shaped structure, as shown in FIGS. 4c and 4d. With this design, the length of the valve clip when in a preloaded state can be shortened.

In this embodiment, the linking member 3 is provided with an anti-retreat structure 34 which is fitted with the self-locking rod 42. The anti-retreat structure 34 can enhance the stability of the locking device 4 and ensure the locking effect for a long time.

In this embodiment, the anti-retreat structure 34 is screw threads or a recess.

In this embodiment, the push-pull device 9 includes leaflet catching devices 91, a leakage-proof tubular member 5, a first linkage rod 6 and a second linkage rod 7. The first linkage rod 6 and the second linkage rod 7 are hinged to the leakage-proof tubular member 5 and are arranged on left and right sides of the leakage-proof tubular member 5, respectively, and the first linkage rod 6 and the second linkage rod 7 are hinged to the first clamping arm 1 and the second clamping arm 2, respectively. The leaflet catching devices 91 are arranged on the first linkage rod 6 and the second linkage rod 7, respectively. The leaflet catching devices 91 each have a preset shape, and the leaflet catching devices 91 closely fit against the linkage rods, respectively, in a natural state. The leaflet catching devices 91, when being preloaded, always fit against the leakage-proof tubular member 5. When the valve clip catches the leaflets, the leaflet catching devices 91 restore the preset shape to clamp the leaflets.

In this embodiment, an end, connected to the push-pull device 9, of the first long arm 12 is provided with a circular arc-shaped buffer segment 121, as shown in FIGS. 2a and 2b. When the valve clip catches the leaflet and completes the clamping, the circular arc-shaped buffer segment 121 may protect the native leaflet from being injured. It should be noted that, in the FIGS. 2a and 2b, only the first long arm 12 provided with the circular arc-shaped buffer segment 121 is shown as an example, the same arrangement is applied to the second long arm 22.

In this embodiment, the cross section of each of the first long arm 12 and the second long arm 22 is in an internally-concaved shape. With such a design, when the valve clip is in the closed state, the first long arm 12 and the second long arm 22 have a certain wrapping effect on the leakage-proof tubular member 5, so that the leakage-proof effect of the leakage-proof tubular member 5 is better. Moreover, the configuration of the internally concaved shape renders significant reduction of the weight of the first long arm 12 and the second long arm 22, therefore, the slippage of the valve clip in the heart due to the excessive weight is effectively avoided, the stability of anchoring of the valve clip in the heart is facilitated, and the native leaflets may not be excessively torn and the intracardiac tissues may not be injured accordingly.

Figure 5A:
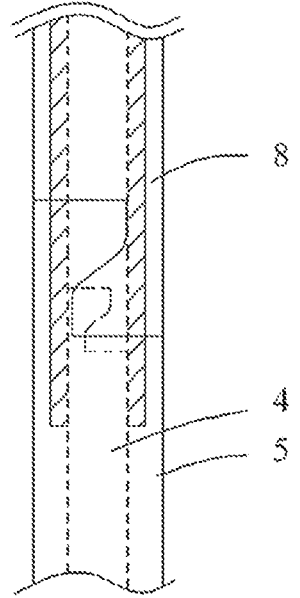
FIGS. 5a~5b are schematic diagrams showing a process in which a delivering catheter is dissembled from a valve clip according to the present application.
Figure 5B:
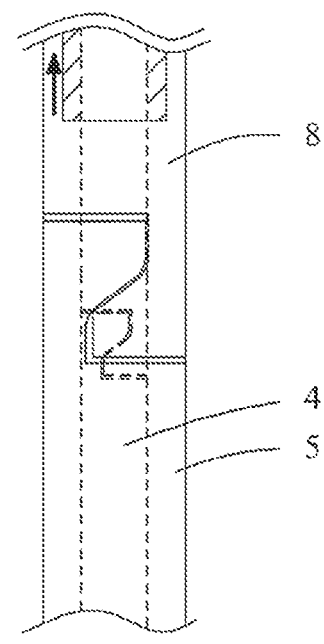

In this embodiment, the valve clip further includes a delivering system for the valve clip, the delivering system for the valve clip includes a control handle and a delivering catheter 8 connected to the control handle, as shown in FIGS. 5a and 5b, a distal end portion of the delivering catheter 8 is detachably connected to the valve clip. When being preloaded, the delivering catheter 8 is connected to the valve clip, and when the valve clip is implanted in a target position, the delivering catheter 8 is separable from the valve clip.

The working principle of the present application is as follows.

Figure 6A:
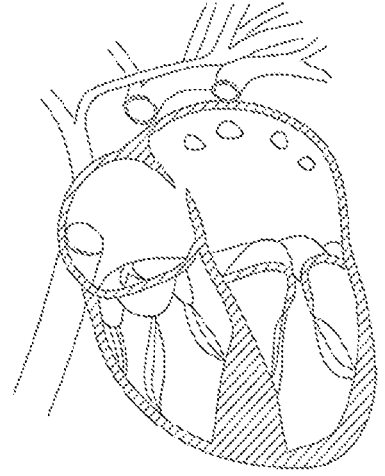
FIGS. 6a~6g are schematic diagrams showing a process in which a delivering catheter enters a heart according to the present application.
Figure 6B:
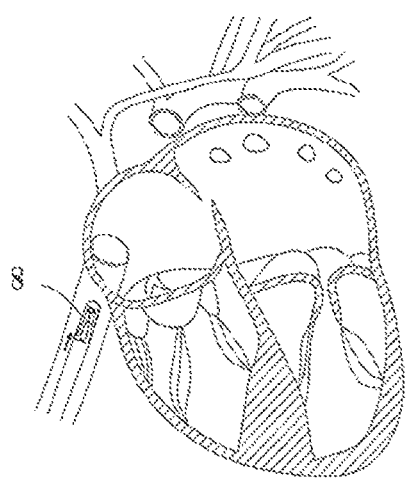
Figure 6C:
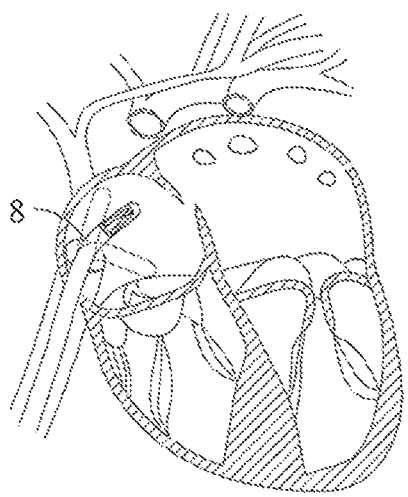
Figure 6D:
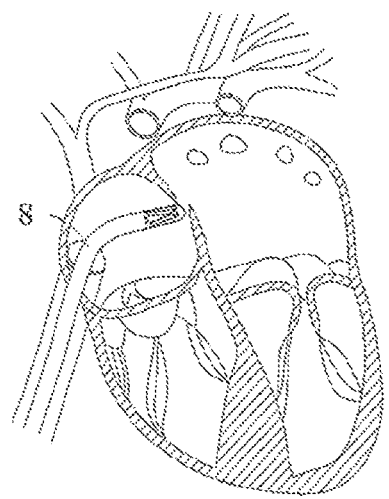
Figure 6E:
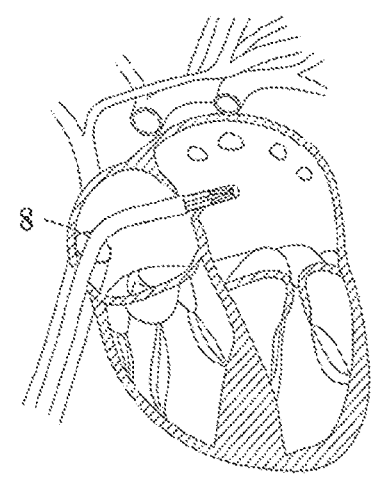
Figure 6F:
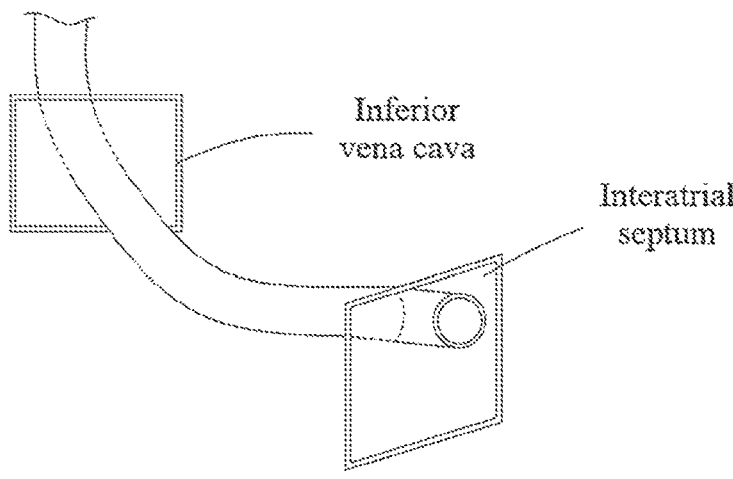
Figure 6G:
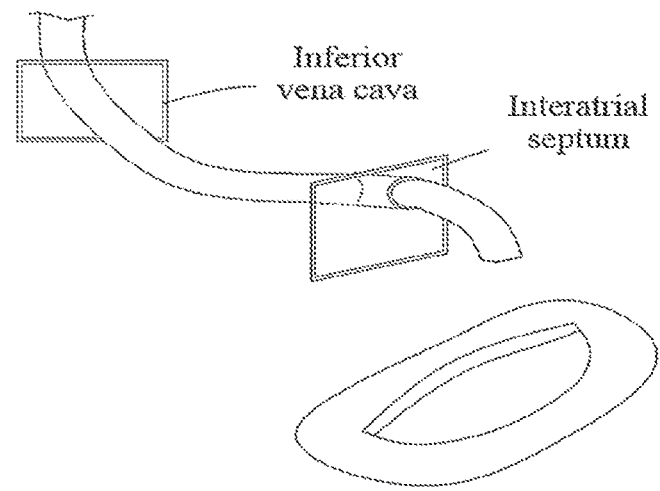

1. The delivering catheter 8 of the valve clip is operated to enter the heart from the inferior vena cava, and then the delivering catheter 8 is operated to cause the valve clip to pass through the interatrial septum, as shown in FIGS. 6a, 6b, 6c, 6d and 6e. The delivering catheter 8 is continued to be operated to bend to allow the valve clip to directly face the mitral valve, as shown in FIGS. 6f and 6g.

Figure 7A:
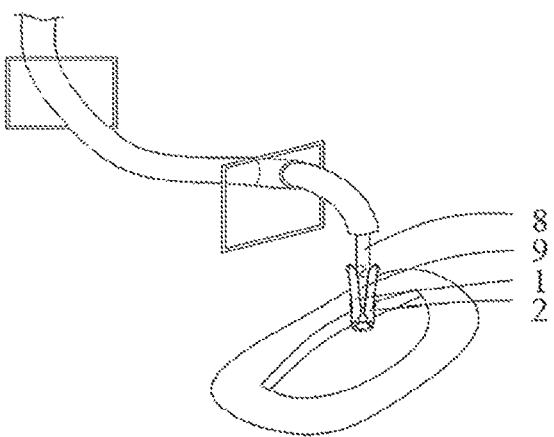
FIGS. 7a~7c are schematic diagrams showing a process in which a valve clip is opened in a left atrium according to the present application.
Figure 7B:
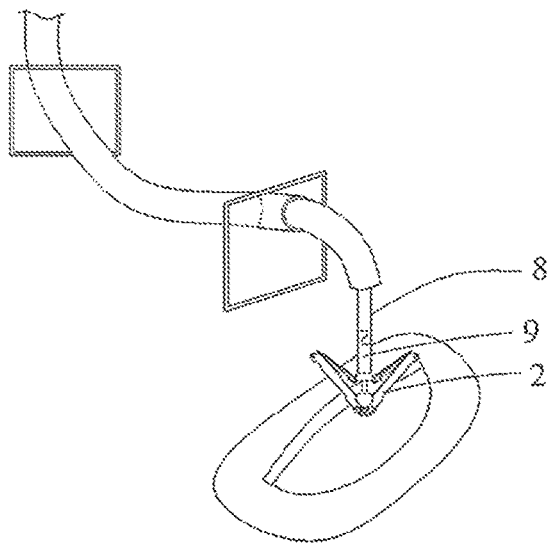
Figure 7C:
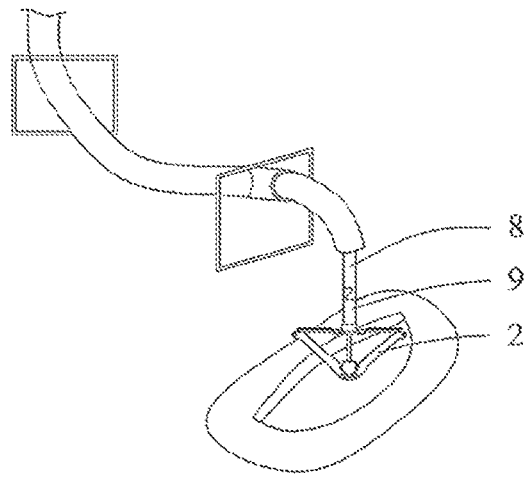

2. The control handle is operated to retract an outer sheath to expose the valve clip in the left atrium, and the control handle is operated to drive the locking device 4 to move distally relative to the leakage-proof tubular member 5 until the opening angle between the first clamping arm 1 and the second clamping arm 2 is at its maximum value, as shown in FIGS. 7a, 7b and 7c.

Figure 8A:
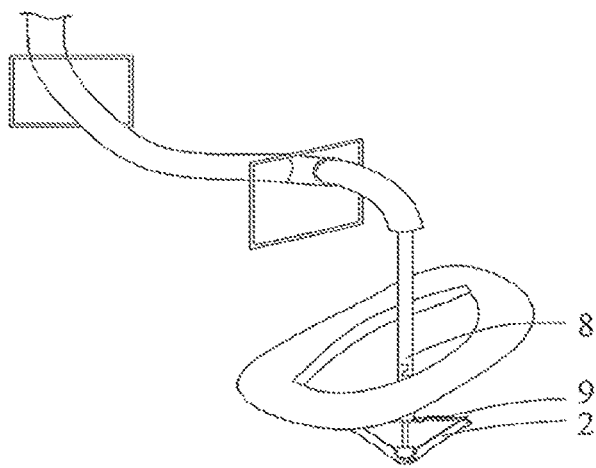
FIGS. 8a~8h are schematic diagrams showing a process in which a valve clip is moved to an optimal valve catching position according to the present application.

3. The control handle is operated to drive the valve clip to pass through the mitral valve, as shown in FIG. 8a, and it is determined through images whether the valve clip is located in an optimal valve clamping position; and if the valve clip is located in the optimal valve clamping position, a step 5 is directly performed; and if the valve clip is not located in the optimal valve clamping position, a step 4 is performed.

Figure 8B:
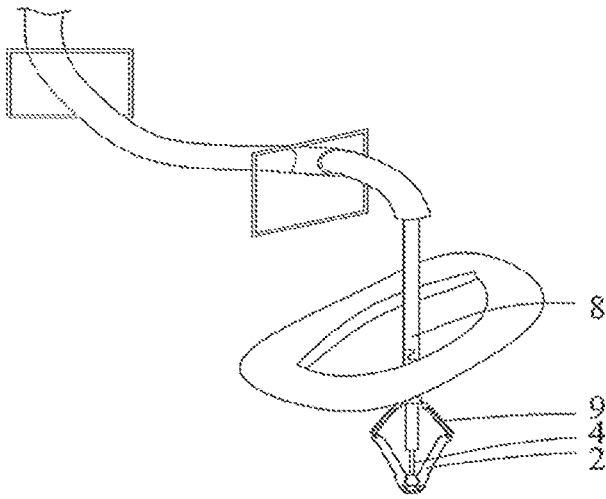
Figure 8C:
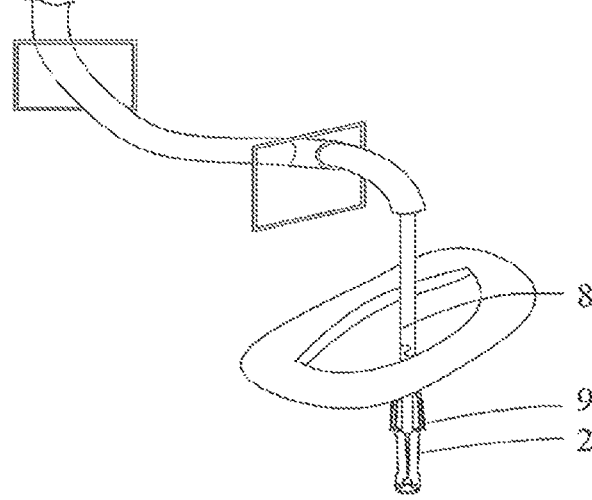
Figure 8D:
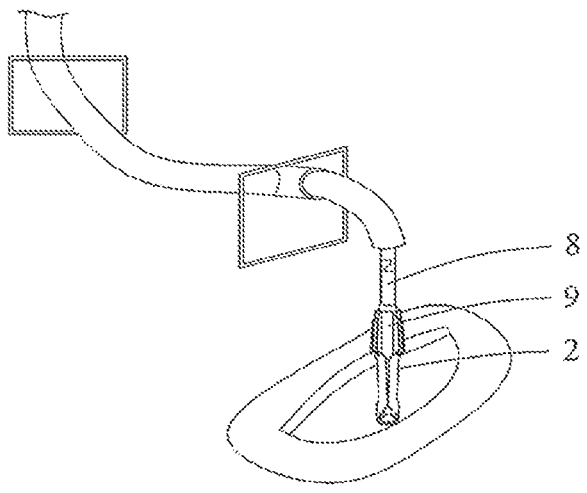
Figure 8E:
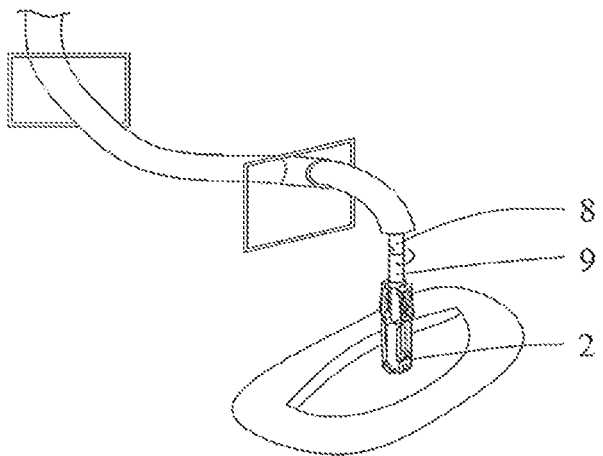
Figure 8F:
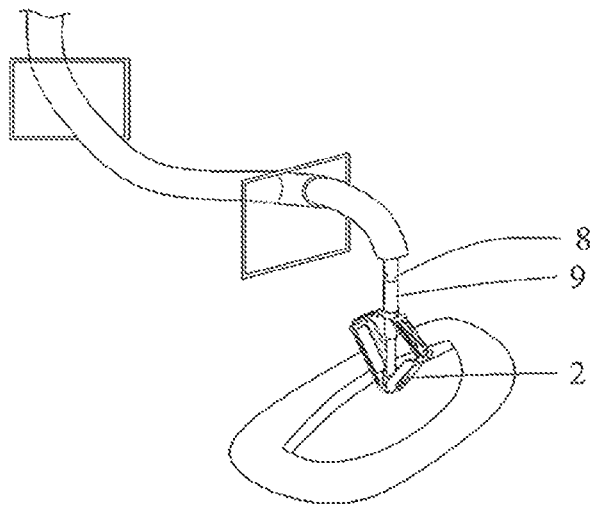
Figure 8G:
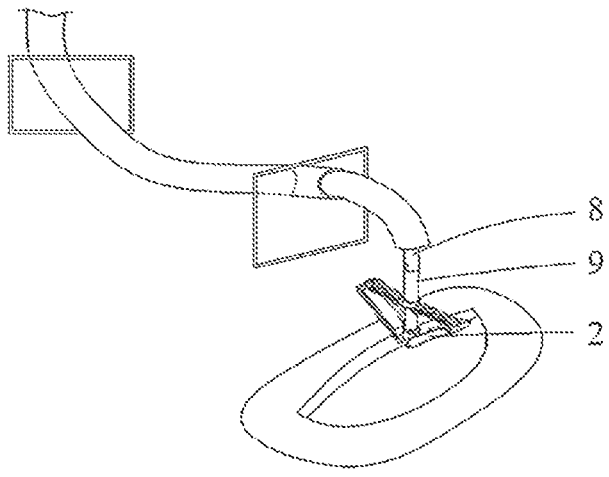
Figure 8H:
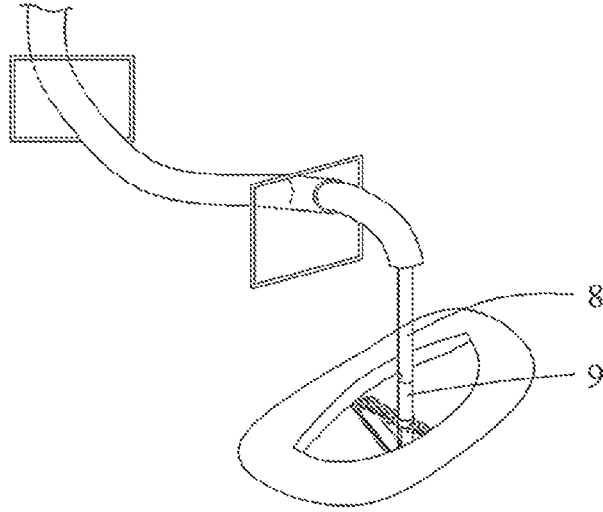

4. The control handle is operated to pull the locking device 4 to the most distal end, and at this time, the radial space occupied by the valve clip is the minimum, and the valve clip is pulled to the left atrium, and as shown in FIGS. 8b, 8c and 8d, the clamping arms and the linkage rods are at obtuse angles, which conforms with the physiological structure and may not damage tissues such as the intracardiac chordae tendineae. The control handle is operated to rotate to deliver the valve clip to the optimal valve clamping position, as shown in FIGS. 8e, 8f, 8g and 8h.

5. The control handle is operated to perform leaflet clamping, to allow the anterior leaflet and the posterior leaflet to enter the leaflet catching devices 91 and be fixed between the leakage-proof tubular member 5 and the first linkage rod 6 and between the leakage-proof tubular member 5 and the second linkage rod 7, respectively.

Figure 1C:
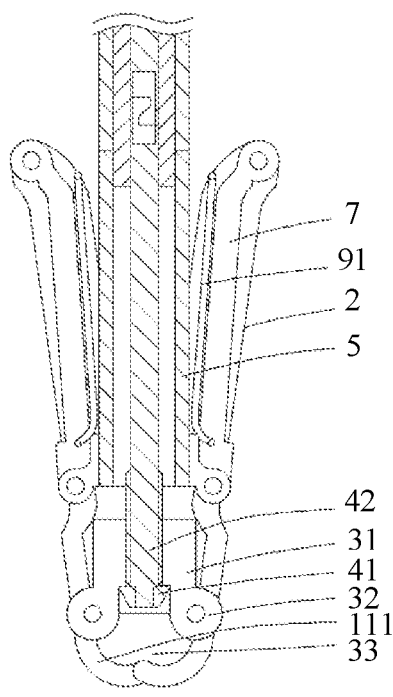

6. The control handle is operated to drive the locking device 4 to move proximally until the opening angle between the first clamping arm 1 and the second clamping arm 2 is at the minimum value, as shown in FIG. 1c.

Figure 1D:
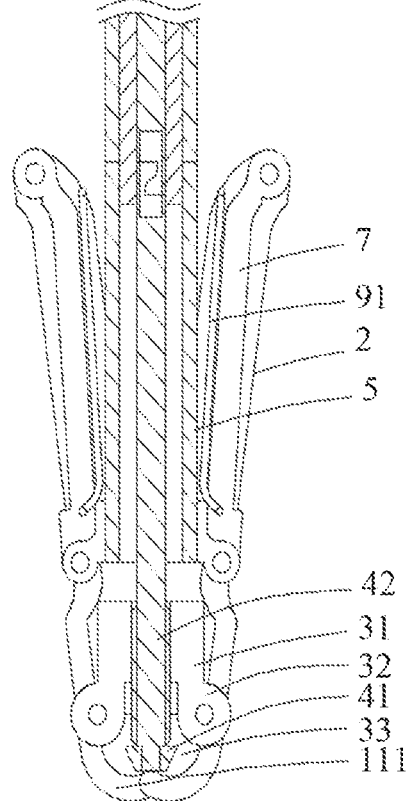

7. The locking device 4 is operated to move distally in an axial direction of the linking member 3 until the locking head 41 abuts against the first locking portion 111 and the second locking portion to lock the valve clip, as shown in FIG. 1d.

8. The control handle is operated to separate the delivering catheter 8 from the valve clip, as shown in FIGS. 5a and 5b, and the delivering catheter 8 is withdrawn from the body.

Second Embodiment

Figure 9A:
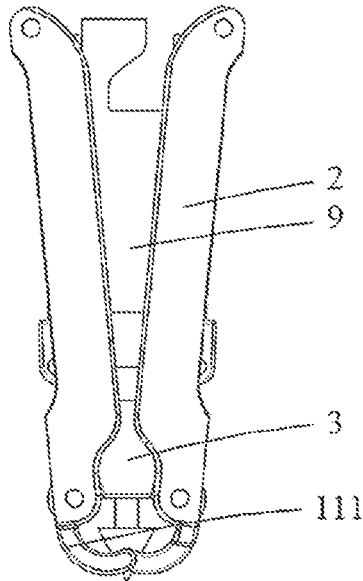
FIGS. 9a~9c are diagrams of another embodiment of a locking device of a valve clip according to the present application.
Figure 9B:
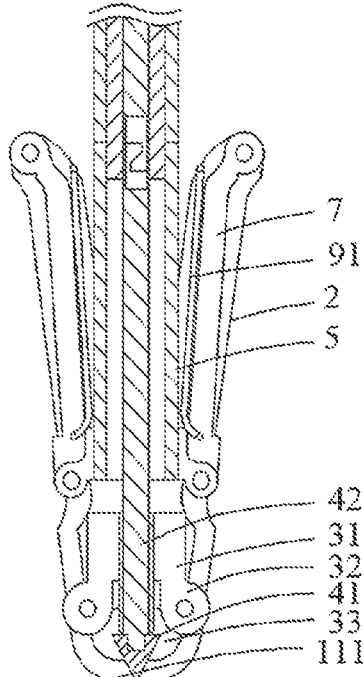

In another embodiment, as shown in FIGS. 9a and 9b, a valve clip having a locking mechanism includes a first clamping arm 1, a second clamping arm 2, a linking member 3 and a locking device 4. The locking device 4 is connected to the linking member 3. The linking member 3 is hinged to each of the first clamping arm 1 and the second clamping arm 2. The first clamping arm 1 includes a first long arm 12 and a first short arm 11 and the second clamping arm 2 includes a second long arm 22 and a second short arm 21, the first short arm 11 drives the first long arm 12 in the manner of levering with a hinge point as a fulcrum, the second short arm 21 drives the second long arm 22 in the manner of levering with a hinge point as a fulcrum, an end of the first short arm 11 is provided with a first locking portion 111, and an end of the second short arm 21 is provided with a second locking portion 211. When an opening angle between the first clamping arm 1 and the second clamping arm 2 becomes larger, the first locking portion 111 of the first clamping arm 1 is buckled with the second locking portion 211 of the second clamping arm 2 in a staggered manner, and when the opening angle between the first clamping arm 1 and the second clamping arm 2 becomes smaller, a locking region 33 is formed between the linking member 3 and the first locking portion 111 and the second locking portion 211, and an end of the locking device 4 enters the locking region 33 and is locked to and fitted with the first locking portion 111 and the second locking portion 211.

The valve clip further includes a push-pull device 9, and the push-pull device 9 includes leaflet catching devices 91, a leakage-proof tubular member 5, a first linkage rod 6 and a second linkage rod 7. The first linkage rod 6 and the second linkage rod 7 are hinged to the leakage-proof tubular member 5 and are arranged on left and right sides of the leakage-proof tubular member 5, respectively, and the first linkage rod 6 and the second linkage rod 7 are hinged to the first clamping arm 1 and the second clamping arm 2, respectively. The leaflet catching devices 91 are arranged on the first linkage rod 6 and the second linkage rod 7 respectively. The leaflet catching devices 91 each have a preset shape, and the leaflet catching devices 91 closely fit against the linkage rods respectively in a natural state. The leaflet catching devices 91, when being preloaded, always fit against the leakage-proof tubular member 5. When the valve clip catches the leaflets, the leaflet catching devices 91 restore the preset shape to clamp the leaflets.

Figure 9C:
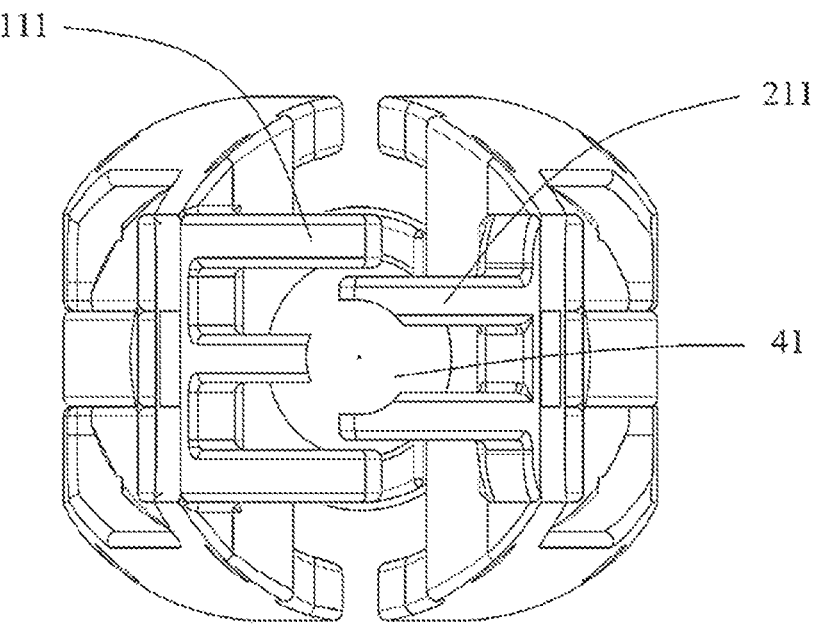

In this embodiment, the locking device 4 is in threaded connection with the linking member 3, and the locking device 4 cannot rotate without being subjected to an external force in the heart, therefore the locking device 4 cannot move axially after abutting against the first locking portion 111 and the second locking portion 211. The first locking portion 111 and the second locking portion 211 receive opposite supporting forces from a radial direction of the locking device 4, respectively, and as shown in FIG. 9c, the first clamping arm 1 receives a leftward radial supporting force, and the second clamping arm 2 receives a rightward radial supporting force, such that the first clamping arm 1 and the second clamping arm 2 cannot be opened. The composition and connection manner of the components of the delivering system for the valve clip having the locking mechanism of the present application are described in detail below with reference to the drawings.

In this embodiment, the first locking portion 111 includes arc-shaped segments 1111. When the opening angle between the first clamping arm 1 and the second clamping arm 2 becomes larger, the first arc-shaped segments 1111 of the first clamping arm 1 are buckled with the second arc-shaped segments 2111 of the second clamping arm 2 in a staggered manner. The first locking portion 111 is designed to be the first arc-shaped segments 1111, which is beneficial to increasing a force arm of the first locking portion 111 and enhancing the acting force of locking, and moreover, the staggered buckled manner is beneficial to saving the space for loading.

In this embodiment, the lengths of the first arc-shaped struts 1112 and the second arc-shaped struts vary from the lengths of the first arc-shaped struts 1112 and the second arc-shaped struts in the previous embodiment. A hole is formed between the first arc-shaped struts 1112 and the second arc-shaped struts when the first clamping arm 1 and the second clamping arm 2 are closed. The locking head 41 of the locking device 4 is configured in a tapered structure, and the diameter of a proximal end portion of the locking head 41 of the locking device 4 is larger than a distance between an end of the first arc-shaped strut 1112 and an end of the second arc-shaped strut. The locking device 4 is operated to drive a distal end portion of the locking head 41 of the locking device 4 to enter/pass through the hole between the first arc-shaped struts 1112 and the second arc-shaped struts, and meanwhile, the locking head 41 also partially abuts against the first arc-shaped struts 1112 and the second arc-shaped struts so as to limit the position and further lock, as shown in FIGS. 9b and 9c.

Third Embodiment

Figure 10A:
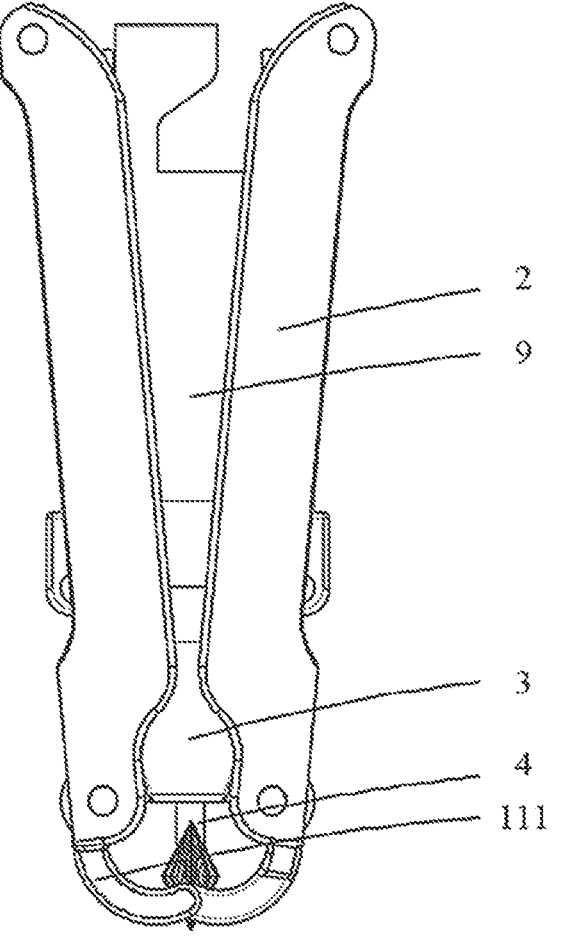
FIGS. 10a~10c are diagrams of another embodiment of a locking device of a valve clip according to the present application.
Figure 10B:
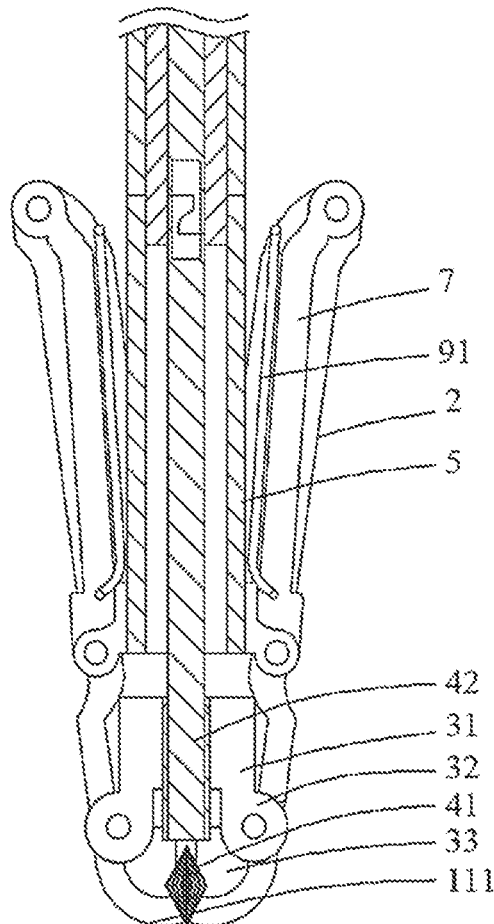

In another embodiment, as shown in FIGS. 10a and 10b, a valve clip having a locking mechanism includes a first clamping arm 1, a second clamping arm 2, a linking member 3 and a locking device 4. The locking device 4 is connected to the linking member 3. The locking device 4 includes a locking head 41 and a self-locking rod 42. The linking member 3 is hinged to each of the first clamping arm 1 and the second clamping arm 2. The first clamping arm 1 includes a first long arm 12 and a first short arm 11 and the second clamping arm 2 includes a second long arm 22 and a second short arm 21, the first short arm 11 drives the first long arm 12 in the manner of levering with a hinge point as a fulcrum, the second short arm 21 drives the second long arm 22 in the manner of levering with a hinge point as a fulcrum, an end of the first short arm 11 is provided with a first locking portion 111, and an end of the second short arm 21 is provided with a second locking portion 211. When an opening angle between the first clamping arm 1 and the second clamping arm 2 becomes larger, the first locking portion 111 of the first clamping arm 1 is buckled with the second locking portion 211 of the second clamping arm 2 in a staggered manner; and when the opening angle between the first clamping arm 1 and the second clamping arm 2 becomes smaller, a locking region 33 is formed between the linking member 3 and the first locking portion 111 and the second locking portion 211, and an end of the locking device 4 enters the locking region 33 and is locked to and fitted with the first locking portion 111 and the second locking portion 211.

The valve clip further includes a push-pull device 9, the push-pull device 9 includes leaflet catching devices 91, a leakage-proof tubular member 5, a first linkage rod 6 and a second linkage rod 7. The first linkage rod 6 and the second linkage rod 7 are hinged to the leakage-proof tubular member 5 and are arranged on left and right sides of the leakage-proof tubular member 5, respectively, and the first linkage rod 6 and the second linkage rod 7 are hinged to the first clamping arm 1 and the second clamping arm 2, respectively. The leaflet catching devices 91 are arranged on the first linkage rod 6 and the second linkage rod 7 respectively. The leaflet catching devices 91 each have a preset shape, and the leaflet catching devices 91 closely fit against the linkage rods respectively in a natural state. The leaflet catching devices 91, when being preloaded, always fit against the leakage-proof tubular member 5. When the valve clip catches the leaflets, the leaflet catching devices 91 restore the preset shape to clamp the leaflets.

Figure 10C:
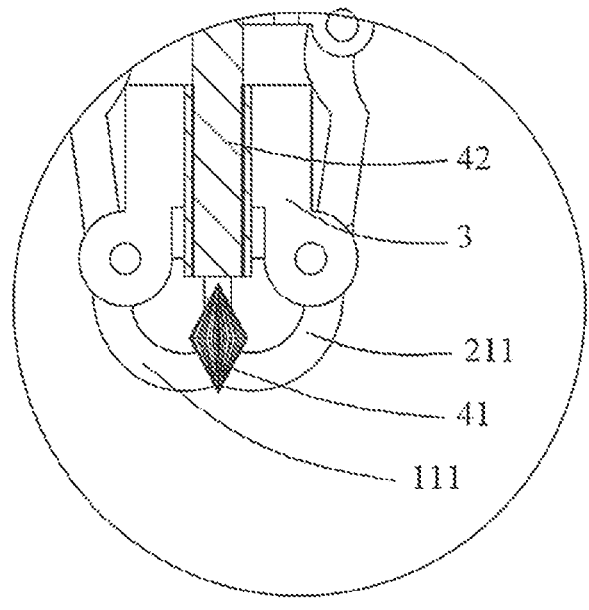

In this embodiment, the self-locking rod 42 is in threaded connection with the linking member 3, and the locking device 4 cannot rotate without being subjected to an external force in the heart, therefore the locking head 41 cannot move axially after abutting against the first locking portion 111 and the second locking portion 211. The first locking portion 111 and the second locking portion 211 receive opposite supporting forces from a radial direction of the locking head 41, respectively and as shown in FIG. 10c, the first clamping arm 1 receives a leftward radial supporting force, and the second clamping arm 2 receives a rightward radial supporting force, such that the first clamping arm 1 and the second clamping arm 2 cannot be opened. The composition and connection manner of the components of the delivering system for the valve clip having the locking mechanism of the present application are described in detail below with reference to the drawings.

Different from the above-described embodiments, in this embodiment, the locking head 41 is a stent-shaped self-expansion structure, and the locking head 41 is fitted with the first locking portion 111 and the second locking portion 211 to be locked to the first locking portion 111 and the second locking portion 211.

In this embodiment, the locking head 41 may be a tapered structure, or a shuttle-shaped structure, or a diamond-shaped structure, or a prismatic structure, or an arrow-shaped structure, and a distal end portion of the locking head 41 is a tapered structure.

In this embodiment, the locking head 41 is configured to be a diamond-shaped structure, the locking head 41 is configured to be hollow, the locking head 41 is made of an elastic metal material, and is formed therein with a hollow region, and the hollow region serves as a buffer region. After the valve clip is implanted into the heart, the first clamping arm and the second clamping arm are subjected to a certain degree of stress due to the compression and relaxation of the heart valve itself, whereby the degrees of closing between the push-pull device and the first clamping arm and between the push-pull device and the second clamping arm are adversely affected, and a certain degree of regurgitatively flowing occurs. In the case where the locking head 41 is made of the elastic metal material and the locking head 41 is formed therein with the buffer region, the first long arm 12 of the first clamping arm and the second long arm 22 of the second clamping arm are subjected to a stress caused by the movement of the valve itself and then the stress is transferred to the first short arm 11 and the second short arm 21, and subsequently the stress applied to the first short arm 11 and the second short arm 21 is transferred to the locking head 41, whereby the locking head 41 is deformed in a certain degree, and breaks down the stress received by it, thereby always guaranteeing the clamping force and the tightness between the push-pull device 9 and the first clamping arm and the second clamping arm, and avoiding the regurgitation.

In this embodiment, the first locking portion 111 includes multiple first arc-shaped struts 1112, the second locking portion 211 includes multiple second arc-shaped struts, and when the opening angle between the first clamping arm 1 and the second clamping arm 2 becomes larger, the first arc-shaped struts 1112 of the first clamping arm 1 are buckled with the second arc-shaped struts of the second clamping arm 2 in a staggered manner; and the multiple first arc-shaped struts 1112 and second arc-shaped struts facilitate increasing force action points of the first short arm 11 and second short arm 21, so that the locking is more stable and reliable.

Fourth Embodiment

Figure 11A:
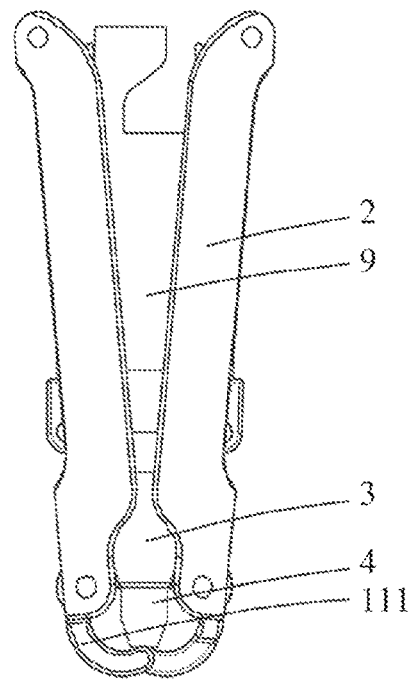
FIGS. 11a~11g are diagrams of another embodiment of a locking device of a valve clip according to the present application.
Figure 11B:
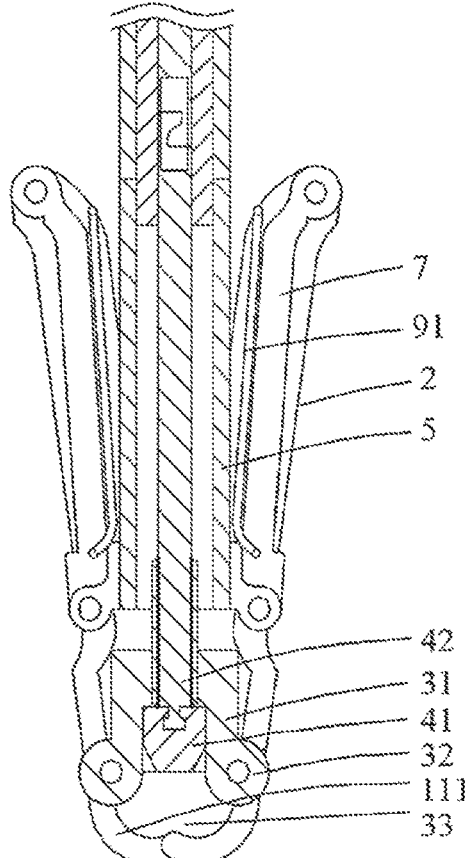
Figure 11C:
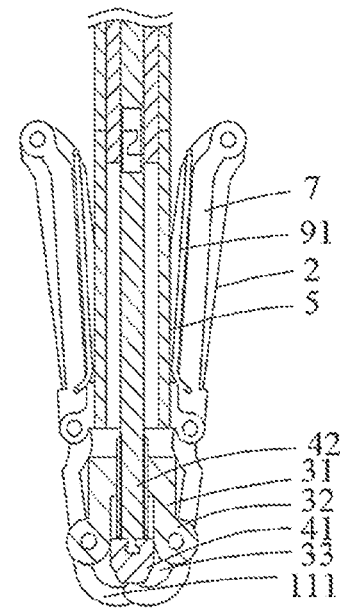

In another embodiment, as shown in FIGS. 11a and 11c, a valve clip having a locking mechanism includes a first clamping arm 1, a second clamping arm 2, a linking member 3 and a locking device 4. The locking device 4 is connected to the linking member 3. The locking device 4 includes a locking head 41 and a self-locking rod 42. The linking member 3 is hinged to each of the first clamping arm 1 and the second clamping arm 2. The first clamping arm 1 includes a first long arm 12 and a first short arm 11 and the second clamping arm 2 includes a second long arm 22 and a second short arm 21, the first short arm 11 drives the first long arm 12 in the manner of levering with a hinge point as a fulcrum, the second short arm 21 drives the second long arm 22 in the manner of levering with a hinge point as a fulcrum, an end of the first short arm 11 is provided with a first locking portion 111, and an end of the second short arm 21 is provided with a second locking portion 211. When an opening angle between the first clamping arm 1 and the second clamping arm 2 becomes larger, the first locking portion 111 of the first clamping arm 1 is buckled with the second locking portion 211 of the second clamping arm 2 in a staggered manner, and when the opening angle between the first clamping arm 1 and the second clamping arm 2 becomes smaller, a locking region 33 is formed between the linking member 3, the first locking portion 111 and the second locking portion 211, and an end of the locking device 4 enters the locking region 33 and is locked to and fitted with the first locking portion 111 and the second locking portion 211.

The valve clip further includes a push-pull device 9, and the push-pull device 9 includes leaflet catching devices 91, a leakage-proof tubular member 5, a first linkage rod 6 and a second linkage rod 7. The first linkage rod 6 and the second linkage rod 7 are hinged to the leakage-proof tubular member 5 and are arranged on left and right sides of the leakage-proof tubular member 5, respectively, and the first linkage rod 6 and the second linkage rod 7 are hinged to the first clamping arm 1 and the second clamping arm 2, respectively. The leaflet catching devices 91 are arranged on the first linkage rod 6 and the second linkage rod 7 respectively. The leaflet catching devices 91 each have a preset shape, and the leaflet catching devices 91 closely fit against the linkage rods respectively in a natural state. The leaflet catching devices 91, when being preloaded, always fit against the leakage-proof tubular member 5. When the valve clip catches the leaflets, the leaflet catching devices 91 restore the preset shape to clamp the leaflets.

Figure 11D:
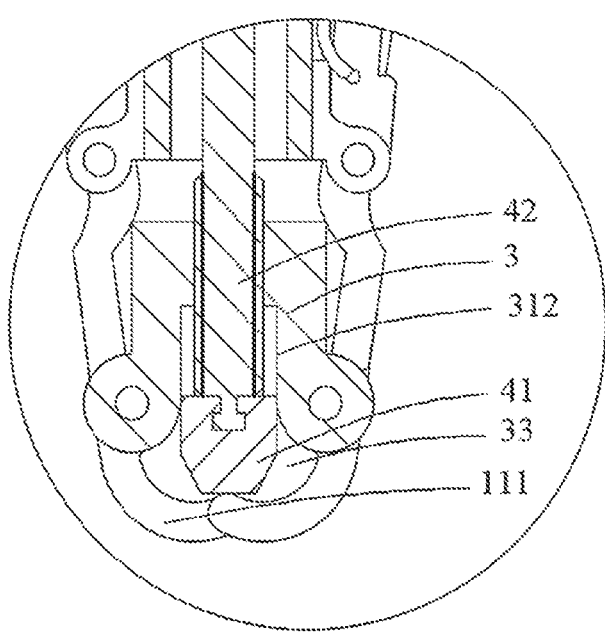

In this embodiment, a rotatable structure 43 is provided between the self-locking rod 42 and the locking head 41 to enable the self-locking rod 42 and the locking head 41 to rotate relative to each other, as shown in FIG. 11*d*.

In this embodiment, the rotatable structure 43 includes a groove 431 and a boss 432, the groove 431 is arranged at a proximal end of the locking head 41, the boss 432 is arranged at a distal end of the self-locking rod 42, and the groove 431 is fitted with the boss 432, as shown in FIG. 11*d*.

In this embodiment, the linking member 3 is provided with a mounting recess 312, at least part of the locking head 41 is always arranged within the mounting recess 312, and the mounting recess 312 is arranged to restrict the locking head from rotating in a circumferential direction.

Figure 11E:
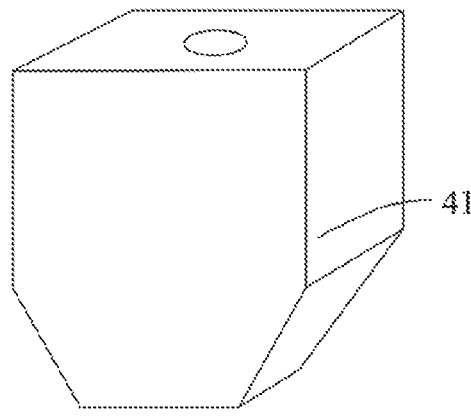
Figure 11F:
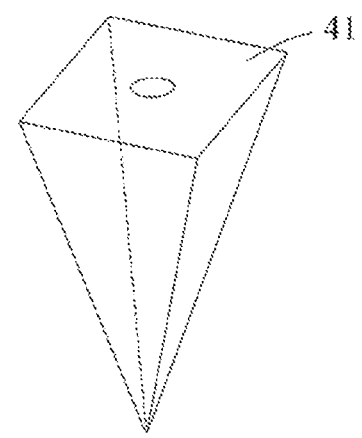
Figure 11G:
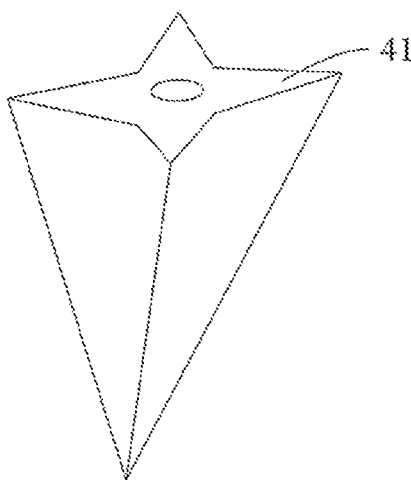

In this embodiment, the shape of the mounting recess 312 matches the shape of the locking head 41, and the locking head 41 is a tapered structure, or a wedge-shaped structure, or a shuttle-shaped structure, or an arrow-shaped structure, as shown in FIGS. 11*e*, 11*f* and 11*g*.

In this embodiment, the linking member 3 includes a linking block 31 and connection lugs 32 arranged on the linking block 31. The linking block 31 is connected to the locking device 4, and the connection lugs 32 are hinged to the first clamping arm 1 and the second clamping arm 2, respectively. The linking block 31 is provided with a through hole 311 and the mounting recess 312 in an axial direction, and the mounting recess 312 is arranged on a distal end side of the through hole 311. In the case where the linking member 3 is provided with the mounting recess 312, the weight of the valve clip may be reduced, whereby the valve clip is effectively prevented from slipping in the heart due to excessive weight, and the stability of anchoring the valve clip in the heart is facilitated.

In this embodiment, the connection lugs 32 are symmetrical about a central axis of the linking block 31.

In this embodiment, the linking block 31 is provided with the mounting recess 312, at least part of the locking head 41 is always arranged within the mounting recess 312, and the mounting recess 312 is arranged to restrict the locking head 41 from rotating in the circumferential direction. When preloaded, the locking head 41 is completely located within the mounting recess 312, so that the space for loading may be saved. When the locking head 41 is fitted with and locked to the first locking portion 111 and the second locking portion 211, the locking head 41 is still partially arranged within the mounting recess 312. With this design, in a case where the locking head 41 is configured to be an irregular-shaped structure, in the process that the self-locking rod 42 is operated to drive the locking head 41 to move axially till being fitted with and locked to the first locking portion 111 and the second locking portion 211, the mounting recess 312 restricts the locking head 41 from rotating in the circumferential direction, and therefore the locking head 41 enters the locking region 33 according to the predetermined position and is fitted with the first locking portion and the second locking portion.

In this embodiment, the mounting recess 312 is arranged on a distal end side of the through hole 311.

In this embodiment, the locking head 41 is restricted by the mounting recess 312 from moving towards the proximal end, and the mounting recess 312 has a diameter larger than the diameter of the through hole 311.

The foregoing content is merely preferred embodiments of the present application, those of ordinary skill in the art will recognize that variations in the detailed implementation and scope of application will be made in accordance with the ideas of the present application, and the content of this specification should not be construed as limiting the present application.

What is claimed is:

1. A valve clip having a locking mechanism, the valve clip comprising a first clamping arm, a second clamping arm, a linking member, a push-pull device and a locking device, wherein the locking device is partially fitted with the linking member, the locking device comprises a locking head and a self-locking rod, the linking member is hinged to each of the first clamping arm and the second clamping arm, the first clamping arm comprises a first long arm and a first short arm and the second clamping arm comprises a second long arm and a second short arm, and an end of each of the first long arm and the second long arm is hinged to the push-pull device, an end of the first short arm is provided with a first locking portion, and an end of the second short arm is provided with a second locking portion, and wherein when the push-pull device is operated to cause an opening angle between the first long arm of the first clamping arm and the second long arm of the second clamping arm to become larger and be in an open state, the first locking portion of the first clamping arm and the second locking portion of the second clamping arm are partially in a staggered fit state, and when the push-pull device is operated to cause the opening angle between the first long arm of the first clamping arm and the second long arm of the second clamping arm to become smaller and be in a closed state, the locking device is moved to cause the locking head to be fitted with and locked to the first locking portion and the second locking portion; and wherein the first locking portion comprises a plurality of first arc-shaped struts, the second locking portion comprises a plurality of second arc-shaped struts, the first arc-shaped struts and the second arc-shaped struts are distributed in a comb-like shape, and when the opening angle between the first clamping arm and the second clamping arm becomes larger, the first arc-shaped struts of the first clamping arm are fitted with the second arc-shaped struts of the second clamping arm in a staggered manner.

2. The valve clip having a locking mechanism of claim 1, wherein each of the first short arm and the second short arm is in an arc shape or an "L" shape, and when the opening angle between the first clamping arm and the second clamping arm becomes larger, the first locking portion of the first clamping arm is fitted with the second locking portion of the second clamping arm in a staggered manner.

3. The valve clip having a locking mechanism of claim 1, wherein the locking head is a stent-shaped self-expansion structure, and the locking head is fitted with the first locking portion and the second locking portion to be locked to the first locking portion and the second locking portion.

4. The valve clip having a locking mechanism of claim 3, wherein the locking head is a tapered structure, or a shuttle-shaped structure, or a diamond-shaped structure, or a prismatic structure, or an arrow-shaped structure.

5. The valve clip having a locking mechanism of claim 1, wherein a rotatable structure is provided between the self-locking rod and the locking head to enable the self-locking rod and the locking head to rotate relative to each other.

6. The valve clip having a locking mechanism of claim 5, wherein the linking member is provided with a mounting recess, at least part of the locking head is always arranged within the mounting recess, and the mounting recess is arranged to restrict the locking head from rotating in a circumferential direction.

7. The valve clip having a locking mechanism of claim 6, wherein the linking member further comprises a linking block and connection lugs arranged on the linking block, the linking block is connected to the locking device, and the connection lugs are hinged to the first clamping arm and the second clamping arm, respectively.

8. The valve clip having a locking mechanism of claim 7, wherein the connection lugs are axially symmetrical about an axis of the linking block.

9. The valve clip having a locking mechanism of claim 7, wherein the linking block is provided with a through hole in an axial direction, and the mounting recess is arranged on a distal end side of the through hole.

10. The valve clip having a locking mechanism of claim 1, wherein each of the first long arm and the second long arm is provided with a bias structure, the bias structure is arranged to divide the respective first long arm or the respective second long arm into a fit portion and a transmission portion, and when the opening angle between the first long arm of the first clamping arm and the second long arm of the second clamping arm becomes smaller to be in the closed state, the fit portion is located closer to a central axis of the valve clip than the transmission portion.

11. The valve clip having a locking mechanism of claim 1, wherein the linking member is an arc-shaped structure or a "V" shaped structure.

12. The valve clip having a locking mechanism of claim 1, wherein a cross section of each of the first long arm and the second long arm is in an internally-concaved shape.

13. The valve clip having a locking mechanism of claim 1, wherein an end, connected to the push-pull device, of each of the first long arm and the second long arm is provided with a circular arc-shaped buffer segment.

14. The valve clip having a locking mechanism of claim 1, wherein a locking region is formed between the linking member, the first locking portion and the second locking portion, and a size of the locking region changes with the opening angle between the first long arm of the first clamping arm and the second long arm of the second clamping arm.

15. The valve clip having a locking mechanism of claim 14, wherein the locking region becomes larger when the opening angle between the first long arm of the first clamping arm and the second long arm of the second clamping arm becomes smaller.

16. The valve clip having a locking mechanism of claim 1, wherein the linking member is provided with an anti-retreat structure which is fitted with the self-locking rod, and the anti-retreat structure is screw threads or a recess.

17. The valve clip having a locking mechanism of claim 1, wherein the locking head is configured to be hollow, and the locking head is made of an elastic metal material.

18. The valve clip having a locking mechanism of claim 1, wherein the push-pull device comprises leaflet catching devices, a leakage-proof tubular member, and a first linkage rod and a second linkage rod, the first linkage rod and the second linkage rod are hinged to the leakage-proof tubular member and are arranged on left and right sides of the leakage-proof tubular member, respectively, the first linkage rod and the second linkage rod are hinged to the first clamping arm and the second clamping arm, respectively, and the leaflet catching devices are arranged on the first linkage rod and the second linkage rod respectively.

* * * * *